US006277557B1

(12) United States Patent
Burger et al.

(10) Patent No.: US 6,277,557 B1
(45) Date of Patent: \*Aug. 21, 2001

(54) INFUSIBLE GRADE SHORT-TERM CELL STORAGE MEDIUM

(75) Inventors: Scott Robert Burger, Shoreview; Allison Hubel, St. Paul; John Jeffrey McCullough, Edina, all of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,810

(22) Filed: Aug. 18, 1999

Related U.S. Application Data

(63) Continuation of application No. 08/955,849, filed on Oct. 21, 1997, now Pat. No. 5,955,257.

(51) Int. Cl.[7] ........................................................ C12N 5/00
(52) U.S. Cl. ............................. 435/2; 435/325; 435/407; 436/18
(58) Field of Search ................................ 435/2, 325, 407; 436/18

(56) References Cited

U.S. PATENT DOCUMENTS

| 4,386,069 | 5/1983 | Estep ..................................... 424/101 |
| 4,663,289 | 5/1987 | Veech ..................................... 435/325 |
| 4,961,928 | 10/1990 | Holme et al. ........................ 424/533 |
| 5,061,620 | 10/1991 | Tsukamoto et al. ................ 435/7.21 |
| 5,422,261 | 6/1995 | Lee et al. ............................. 435/219 |
| 5,580,714 | 12/1996 | Polovina ................................... 435/2 |
| 5,955,257 | * 9/1999 | Burger et al. ............................. 435/2 |

FOREIGN PATENT DOCUMENTS

0356257B1    3/1995   (EP) .

OTHER PUBLICATIONS

"Standards for Hematopoietic Progenitor Cell Collection, Processing and Transplantation", *Foundation for the Accreditation of Hematopoietic Cell Therapy*, 1st edn., 1–58, (Sep. 1996).

Ager, S., et al., "The use of non–cryopreserved peripheral blood progenitor cells in autologous transplantation", *Bone Marrow Transplantation*, 16, 633–34, (1995).

Ahmed, T., et al., "Marrow Storage Techniques: a Clinical Comparison of Refrigeration versus Cyropreservation", *Acta Haematol*, 173–178, (1991).

Ahmed, T., et al., "Refrigeration Storage of Bone Marrow", *Bone Marrow and Stem Cell Processing: A Manual of Current Techniques*, 332–334.

Anderlini, et al., "Clinical Toxicity and Laboratory Effects of Granulocyte–Colony–Stimulating Factor (Filgrastim) Mobilization and Blood Stem Cell Apheresis from Normal Donors, and Analysis of Charges for the Procedures", *Transfusion*, 36, 590–595, (Jul. 1996).

Areman, et al., "Processing and Storage of Human Bone Marrow; A Survey of Current Practices in North America", *Bone Marrow Transplant*, 6, 203–209, (1990).

Areman, et al., "Use of Licensed Electrolyte Solution as an Alternative to Tissue Culture Medium for Bone Marrow Collection", *Transfusion*, 33, 562–566, (1993).

Areman, et al., "Use of Licensed Electrolyte Solutions and Anticoagulant Citrate Dextrose for Bone Marrow Collection", *Advances in Bone Marrow Purging and Processing*, 353–359, (1992).

Areman, E., "Technical Topics", *Ishage Telegraft*, 6–7, (Oct. 1997).

Beaujean, F., et al., "Characteristics of Peripheral Blood Progenitor Cells Frozen After 24 hours of liquid storage", *Journal of Hematotheraphy*, 681–686, (1996).

Bezwoda, W.R., et al., "Non–cryopreserved, limited number (1 or 2) peripheral blood progenitor cell (PBPC) collections following GCSF administration provide adequate hematologic support for high dose chemotherapy", *Hematological Oncology*, 12, 101–110, (1994).

Burger, S.R., et al., "Development of an infusible–grade hematopoietic cell storage solution", From the Dept. of Laboratory Medicine and Pathology, The University of Minnesota Medical School, Minneapolis, MN, 1–49, (1998).

Burnett, A.K., et al., "Haematological reconstitution following high dose and supralethal chemo–radiotheraphy using stored, non–cryopreserved autologous bone marrow", *British Journal of Haematology*, 54, 309–316, (1983).

Carella, A.M., et al., "Massive Chemotherapy with non–Frozen Autologous Bone Marrow Transplantation in 13 Cases of Refractory Hodgkin's Disease", *Eur J Cancer Clin Oncol*, 21, 607–813, (1985).

Carey, P., et al., "Autologous Bone Marrow Transplantation for High–Grade Lymphoid Malignancy Using Melphalan/Irradiation Conditioning Without Marrow Purging or Cryopreservation", *Blood*, 77, 1593–1598, (Apr. 1, 1991).

D'Amico, E.A., et al., "Bone Marrow harvesting from hemophilia A donor", *The Lancey*, 254, (Jan. 23, 1993).

Delforge, A., et al., "Granuloucyte–macrophage progenitor cell preservation at 4 degree C", *British Journal of Haematology*, 49–54, (1983).

(List continued on next page.)

*Primary Examiner*—Leon B. Lankford, Jr.
(74) *Attorney, Agent, or Firm*—Schwegman, Lundberg, Woessner & Kluth, P.A.

(57) ABSTRACT

An infusible-grade storage medium that is capable of preserving the viability and function of stem cells, nucleated cells and other hematopoietic cells is provided.

25 Claims, 11 Drawing Sheets

OTHER PUBLICATIONS

Ende, N., et al., "Potential effectiveness of stored cord blood (non–frozen) for emergency use", *The Journal of Emergency Medicine*, 14, 673–677, (1996).

Gutensohn, K., et al., "Storage of Peripheral Blood Stem Cell Samples Alters Flow Cytometric CD34+ Results", *Beitr Infusionether Transfusionsmed.*, 170–174, (1996).

Hechler, G., et al.. "Storage of noncryopreserved peripheral blood stem cells for transplantation", *Ann Hematol*, 72, 303–306, (1996).

Issaragrisil, S., et al., "Preservation of Haemopoietic Progenitor Cells", *Transplantation*, 36, 341–3, (1983).

Janssen, W.E., et al., "Shipping of Freshly Harvested Bone Marrow", *Bone Marrow and Stem Cell Processing: A Manual of Current Techniques*, 445–448.

Jestice, H.K., et al., "Liquid storage of peripheral blood progenitor cells for transplantation", *Bone Marrow Transplantation*, 14, 991–994, (1994).

Jones, N., et al., "High–dose Melphalan Followed by Autograft Employing Non–cryopreserved Peripheral Blood Progenitor Cells in Children", *European Journal of Cancer*, 32, 1938–1942, (1996)

Killian, D., et al., "A cost–effective and Food and Drug Administration–approved alternative to tissue culture media in cryopreservation", *Transfusion*, 36, 476, (1996).

Kohsaki, et al., "Non–Frozen Preservation of Committed Hematopoietic Stem Cells from Normal Human Bone Marrow", *Stem Cells*, 1, 111–123, (1981).

Lasky, et al., "Liquid Storage of Unseparated Human Bone Marrow : Evaluation of Hematopoietic Progenitors by Clonal Assay", *Transfusion*, 26 vol. 4, 331–334, (1986).

Lennard, A.L., et al., "Peripheral blood stem–cell transplantation versus non–cryopreserved autologous bone–marrow transplantation", *The Lancey*, 254, (Jan. 23, 1993).

Mangalik, et al., "Liquid Storage of Bone Marrow", *Experimental Hematology*, 7, 76–94, (1979).

Millar, J.L., et al., "The Viability of Marrow Stored at 4 Degree C", *Autologous Bone Marrow Transplantion and Solid Tumors*, edited by J.G. McVie, et al., 9–12, (1984).

Murea, S., et al., "Granulocytes Harvested Following G–CSF–Enhanced Leukocyte Recovery Retain Their Functional Capacity During In Vitro Culture for 72 Hours", *Journal of Hematotheraphy*, 5, 351–357, (1996).

Niskanen, "Preservation of Human Granulopoietic Precursors Following Storage in the Nonfrozen State", *Transplantation*, 36, 341–343, (1983).

Pettengell, R., et al., "Viability of haemopoietic progenitors from whole bolld, bone marrow and leukapheresis product: effects of storage media, temperature and time", *Bone Marrow Transplantation*, 14, 703–709, (1994).

Phillips, G., et al., "American Society for Blood and Marrow Transplantation Guidelines for Clinical Centers", *Biology of Blood and Marrow Transplantation*, 1, 54–55, (1995).

Preti, R.A., et al., "Clinical and laboratory comparison study of refrigerated and cryopreserved bone marrow for transplantation", *Bone Marrow Transplantation*, 13, 253–260, (1994).

Robinson, W.A., "Autologous Nonfrozen Bone Marrow Transplantation for Intensive Chemotherapy: a Pilot Study", *Acta Haemat 66*, 145–15, (1981).

Rossi, et al., In: *Principles of Transfusion Medicine*, Williams and Wilkins Publishers; Baltimore, Maryland, (1990).

Ruiz–Arguelles, G.J., et al., "Filgrastim–mobilized peripheral–blood stem cells can be stored at 4 degrees and used in autografts to rescue high–dose chemotherapy", *American Journal of Hematology*, 48, 100–103, (1995).

Stroncek, et al., "Treatment of Normal Individuals with Granulocyte–Colony–Stimulating Factor: Donor Experiences and the Effects on Peripheral Blood CD34+ Cell Counts and on the Collection of Peripheral Blood Stem Cells", *Transfusion*, 36, 601–610, (Jul. 1996).

Surgrue, M., et al., "The effect of overnight storage of leukapheresis stem cell products (LSCP) on cell viability and cost", Stem Cell Laboratory, Shands Hospital, University of Florida, College of Medicine, Gainesville, Florida.

Tajima, T., "The Effects of Non–cryopreservation on Clony Formation of Committed Progenitor Cells of Bone Marrow", *Tkai J Exp Clin Med*, 15–22, (1988).

Takahashi, M., et al., "Effects of Marrow Storage at 4 Degree C on the Subsequent Generation of Long–term Marrow Cultures", *Experimental Hermatology*, 13, 691–695, (1985).

Thomas, et al., "Technique for Human Marrow Grafting", *BLOOD The Journal of Hematology*, 36, 507–515, (Oct. 1970).

Wells, et al., "Preservation of Granulopoietic Precursors in Nonfrozen, Stored Human Bone Marrow", *Transplantation*, 22, 568–571, (1976).

* cited by examiner

INFUSIBLE GRADE SHORT-TERM CELL STORAGE MEDIUM

This application is a Continuation of U.S. application Ser. No. 08/955,849 filed Oct. 21, 1997 now U.S. Pat. No. 5,955,257.

BACKGROUND OF THE INVENTION

An estimated 8,000 transplants of marrow, peripheral blood stem cells and umbilical cord blood stem cells took place in 1996. Additional indications for transplantation of hematopoietic stem cells are continually being reported, steadily increasing the number and frequency of transplants. The complexity of cell processing for transplantation also continues to grow and evolve rapidly, often resulting in longer processing times and necessitating transportation of cells to centers capable of performing more sophisticated cell processing procedures.

Hematopoietic transplantation may involve a donor and recipient treated at different institutions, e.g., allogenic transplantation. For autologous transplants, bone marrow is occasionally sent to a larger hospital for specialized treatment, such as the purging of tumor cells. Occasionally, cells to be transplanted are collected at one hospital, then transported to the transplant institution where the cells undergo processing and transplant. Due to geographic separation between donor and recipient, cells may be in transport for extended periods of time e.g., 36 hours, and sometimes much longer between the cell harvest and arrival at the processing laboratory as many donor programs match donor and recipients in different countries.

Following transport, cells can arrive at a processing laboratory at virtually any hour of the day or night, often with extensive processing still to be performed. The processing laboratory faces two alternatives: (1) to store the cells until daytime staff are available, or (2) to process the cells for transplantation immediately upon receipt. The latter requires 24-hour staffing for the processing laboratory and is clearly not possible at most institutions. The former alternative presents the problem of how to store the cells, in which bags, at what temperature and in which medium or solution. Clinical laboratories in general are neither staffed nor equipped to solve this problem to the satisfaction of transplant clinicians.

Since the publication in 1970 of the Thomas and Storb article on human marrow grafting, tissue culture medium has been used for the collection of transplantable hematopoietic stem cells. (Thomas et al., Blood 36:507–515 (1970)). Presently, cells are transported and stored in solutions composed of tissue culture medium. Several different formulations, most commonly α-MEM, IMDM, and RPMI-1640 are currently in use, although two other media, X-VIVO-10 and AIM-V, are also used less frequently (Areman, et al. Bone Marrow Transplant 6:203–209 (1990); Areman et al., Transfusion 31:724–730 (1991)).

Media currently utilized are designated for in vitro use only and contain combinations of inorganic salts, amino acids, vitamins, sugars, dyes, e.g., phenol red and other constituents not available in U.S.P. grade. These solutions employ a phosphate-based buffering system designed for use in the 5% $CO_2$ atmosphere of a cell culture incubator. Such a buffering system is, however, ineffective at atmospheric $CO_2$ concentrations. Cells stored and transported in these solutions are essentially without environmental pH control. Additionally, none of the media have ever been rigorously tested to determine whether one medium is superior or inferior to the others.

Because of the increasingly widespread use of bone marrow and peripheral blood progenitor cells in the treatment of malignancies and hematopoietic disorders, accrediting and regulatory agencies are developing and issuing standards and guidelines for the preparation of components for transplantation (Phillips et al., Biol Of Blood and Marrow Transpln. 1:54–55 (1995); Standards for hematopoietic progenitor cell collection, processing and transplantation, Foundation for the Accreditation of Hematopoietic Cell Therapy ("FAHCT") 1st edn. (1996)). None of the tissue culture media used in marrow collection have been licensed by the United States Food and Drug Administration for in vivo human use. Other non-licensed agents such as dimethylsulfoxide ("DMSO") and Ficoll-hypaque are also used in the processing and preservation of stem cells and other hematopoietic cells but at this time there are no comparable approved substances with which to replace them.

There is a need for a medium for short-term storage of stem cells, nucleated cells, e.g., mononuclear cells, and other hematopoietic cells prior to, during and after processing or that will permit shipment of cells from a processing center to a transplant center. Thus, an infusible-grade storage medium capable of maintaining cell viability and functional capability would be of great value.

SUMMARY OF THE INVENTION

The present invention provides an infusible-grade storage medium for stem cells, nucleated cells, e.g., mononuclear cells, or other hematopoietic cells, consisting essentially of an electrolyte replenisher base solution selected from the group consisting of lactated Ringer's solution, Hank's Balanced Salt Solution (containing no phenol red), and those solutions sold under the trademarks of PLASMALYTE-A, NORMOSOL-R, VEEN-D, and POLYSAL; about 0.1–10% human serum albumin, and wherein the storage medium is buffered with histidine so that it is maintained at physiological pH. A preferred embodiment of the invention includes a storage medium, wherein the replenisher base solution is lactated Ringer's solution and the storage medium contains about 1–2% human serum albumin and does not contain ficoll-hypaque or constituents of tissue culture media, as these components have not been approved for in vivo human use by the United States Food and Drug Administration ("FDA"), e.g., phenol red and constituents not available in U.S.P. grade.

This invention thus provides a storage medium that does not Contain unwanted tissue culture media components and employs components presently approved for human infusion in other medical applications. The present storage medium is formulated from infusible-grade components only, and is effective to maintain human cell viability, biological activity and function.

By using the storage medium and method provided herein, stem cells, nucleated cells and other hematopoietic cells, can be supported and transported without overt disruption or destruction of the functional, immunophenotypic or morphological characteristics of the ultrastructure of the cells. Cell suspensions can be maintained and stored for extended periods of time, e.g., up to 72 hours and later recovered for therapeutic, e.g., infusion or injection into a patient requiring such therapy, or research purposes.

Thus, another preferred embodiment of the invention includes an infusible-grade storage medium wherein the replenisher base solution is the non-polymeric expander, sold under the trademark PLASMALYTE-A and the storage medium contains about 1–2% human serum albumin.

Within yet another embodiment of the invention, an infusible-grade storage medium further comprises an anticoagulant. Anticoagulants useful in the present invention include heparin, acid citrate dextrose ("ACD"), anticoagulant citrate phosphate dextrose adenine solution ("ACDA"), sodium citrate, citrate phosphate dextrose adenine solution ("CPD"). Although the present invention is exemplified by reference to the foregoing anticoagulants, other representative anticoagulants known in the art can also be employed, see *Remington's Pharmaceutical Sciences,* Mack Publishing Company, 16th edn. (1980). A storage medium of the instant invention can be supplemented with the anticoagulant heparin in a final concentration of about 1–75 units/ml of storage medium. Preferably, heparin is in a final concentration of about 5–50 units/ml of storage medium, and most preferably about 10–20 units/ml of medium. Alternatively, the anticoagulants, ACD, ACDA, CPD or sodium citrate can be employed, wherein these anticoagulants are in a final concentration of about 1.0–10 parts/ml of cell storage medium. (Rossi et al., *Principles of Transfusion Medicine,* Williams & Wilkens publishers (1990)).

A storage medium of the instant invention comprises cells at a concentration of about $1\times10^4$–$5\times10^8$ cells per ml of medium, and preferably about $2$–$5\times10^6$–$1\times10^8$ cells per ml of medium.

Other embodiments of the present invention, provide a method for supporting cells, comprising (a) suspending cells in the present cell storage medium to yield a cell suspension of about $1\times10^4$–$5\times10^8$ cells per ml of medium, and (b) maintaining the cell suspension at a temperature of about 4° to 24° C. to yield a stable cell suspension.

In yet another embodiment of the invention, cells are isolated from a donor sample or a suitable blood product by density gradient separation and further concentrated by centrifugation. At high cell concentrations, e.g., $5\times10^8$ cells/ml of medium, preferably a heparinized phosphate buffered saline wash (PBS) step is employed to remove plasma and prevent in vitro coagulation, followed by suspension of the washed cells in a cell storage medium.

In yet another embodiment, the present invention provides an infusible-grade liquid composition, comprising a suspension of viable stem cells, nucleated cells or other hematopoietic cells in a storage medium consisting essentially of an electrolyte replenisher base solution selected from the group consisting of lactated Ringer's solution, Hank's Balanced Salt Solution (containing no phenol red), and those solutions sold under the trademarks of PLASMALYTE-A, NORMOSOL-R, VEEN-D, and POLYSAL. The storage medium further comprises about 0.1 to 10% human serum albumin, wherein the storage medium is buffered with histidine so that it is maintained at physiological pH.

The experiments described herein involve the storage of cells prior to, during or after processing or transport. Additionally, cells can be subjected to a variety of processing steps including the selection of subpopulations, e.g., $CD34^+$ or elutriation of T-cells, culture and genetic manipulation. The medium of the present invention is also suitable for these applications. Thus, if centralized cell processing is to become feasible, short-term liquid storage of processed cells will be necessary to permit shipment of cells from a processing center to a transplant center. Hence, the infusible-grade cell storage medium of the instant invention capable of maintaining cell viability following positive or negative selection, for example, has enormous value.

Moreover, the experiments herein provide strong evidence that an infusible-grade medium containing lactated Ringer's solution or an equivalent electrolyte replenisher base solution, can effectively maintain cell viability, phenotype and function under storage. Additionally, the experiments herein have demonstrated that preferred storage conditions comprise a storage medium containing a final concentration of about 1–2% HSA, buffered with 50 mM histidine and stored at about 40 C. Storage in bags sold under the trademark CRYOCYTE (Baxter, Fenwal Division, Deerfield, Ill.) or in bags such as, PL2410 or PL3014 bags.

These and other aspects of the present invention will become evident upon reference to the following detailed description and attached drawings.

DETAILED DESCRIPTION OF THE INVENTION

Definitions

Figure 1A:
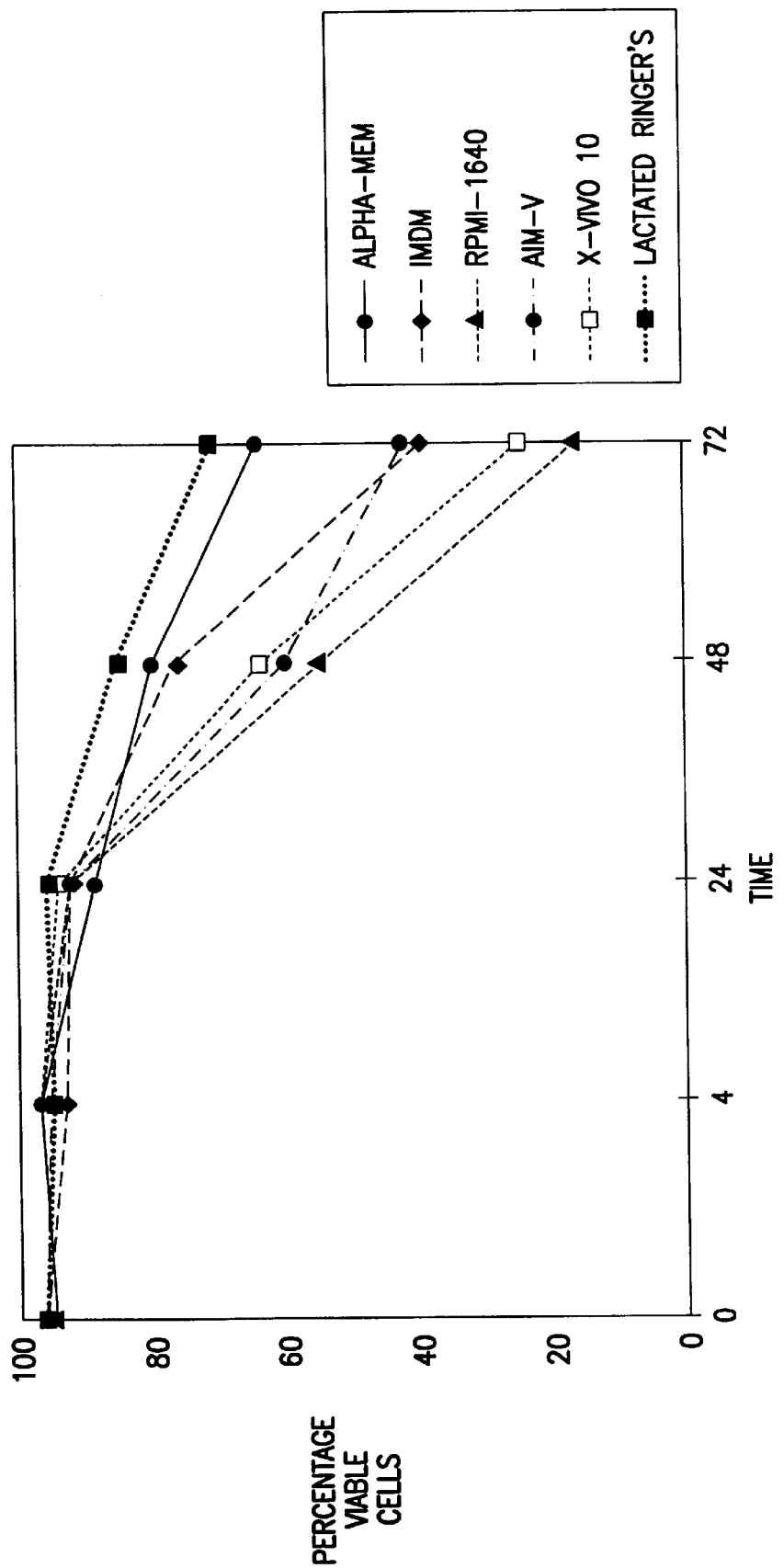
FIG. 1A shows the mean percentage, n=5, of viable nucleated cells in six media (5 tissue culture media and lactated Ringer's solution), maintained at room-temperature (20°–24° C.) having $1\times10^6$ cells/ml of α-MEM, RPMI 1640, IMDM, AIM-V, X-VIVO and lactated Ringer's solution. All media contain about 10% HSA.
Figure 1B:
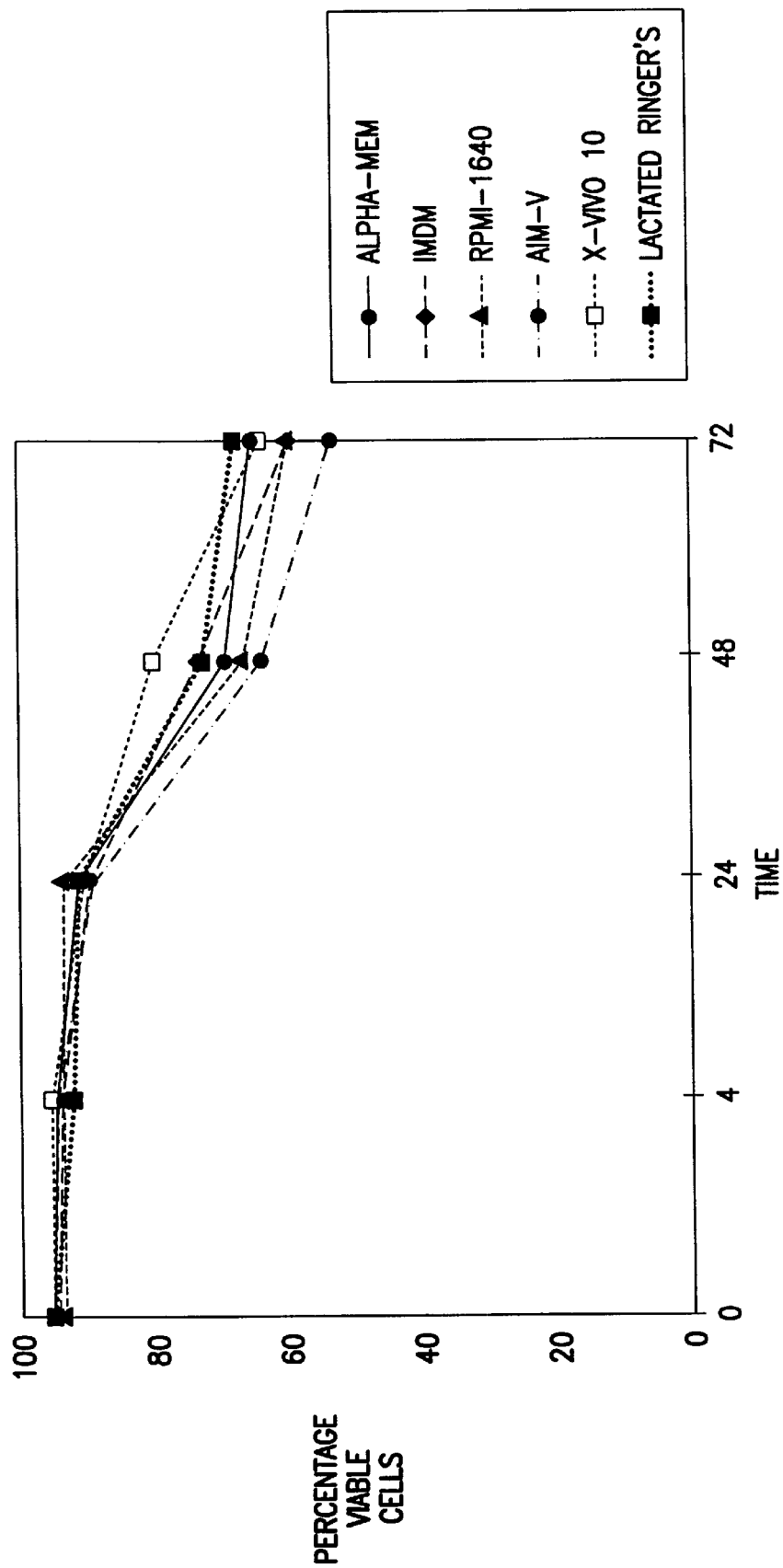
FIG. 1B (shows the mean percentage, n=5, of viable nucleated cells in six media (5 tissue culture media and lactated Ringer's solution), maintained at 4° C., having $1\times10^6$ cells/ml of α-MEM, RPMI 1640, IMDM, AIM-V, X-VIVO and lactated Ringer's solution. All media contain about 10% HSA.
Figure 2A:
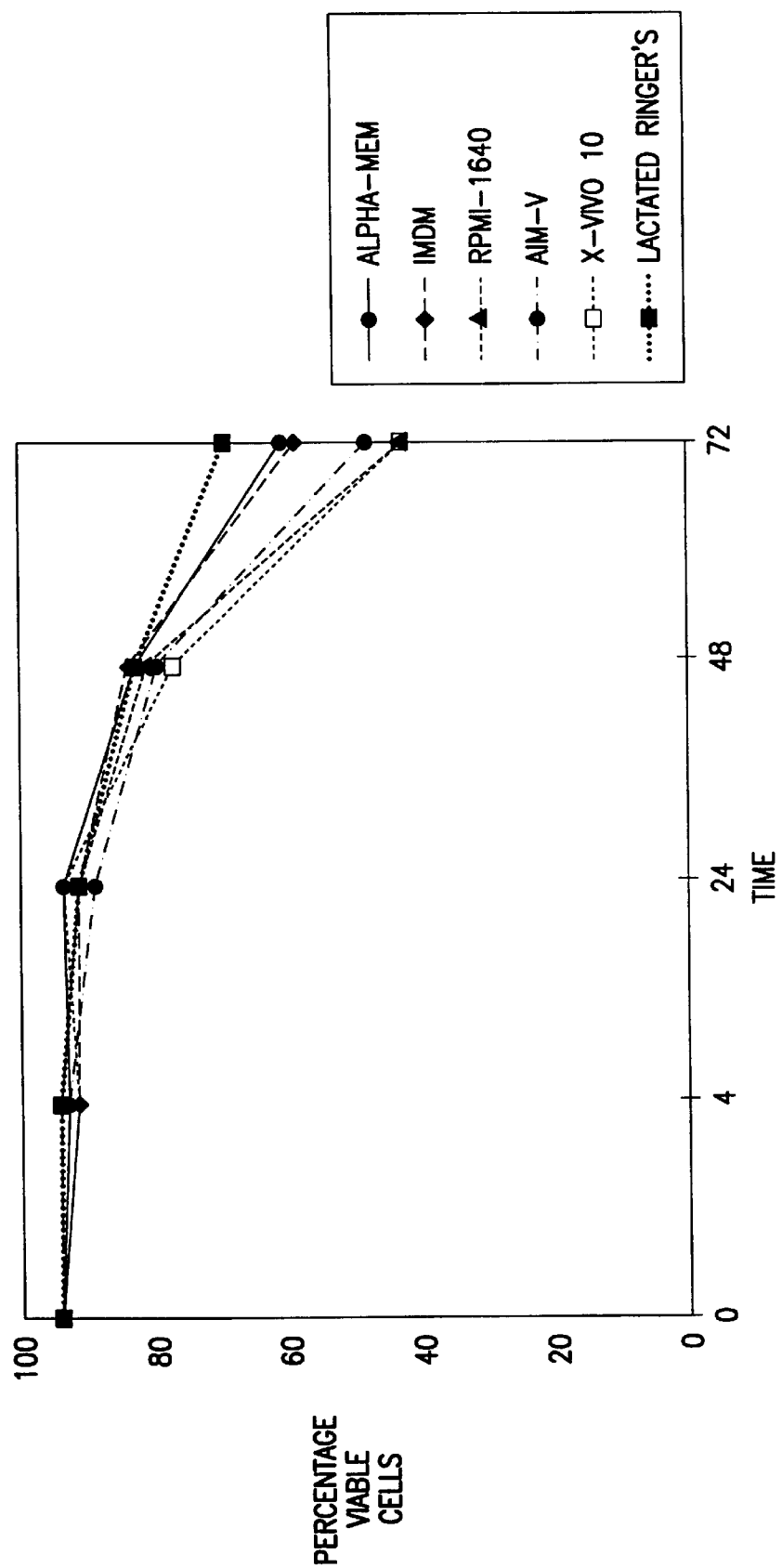
FIG. 2A shows the mean percentage, n=5, of viable nucleated cells in six media (5 tissue culture media and lactated Ringer's solution), maintained at room-temperature (20°–24° C.) having $1\times10^6$ cells/ml of α-MEM, RPMI 1640, IMDM, AIM-V, X-VIVO and lactated Ringer's solution. All media contain about 1% HSA.
Figure 2B:
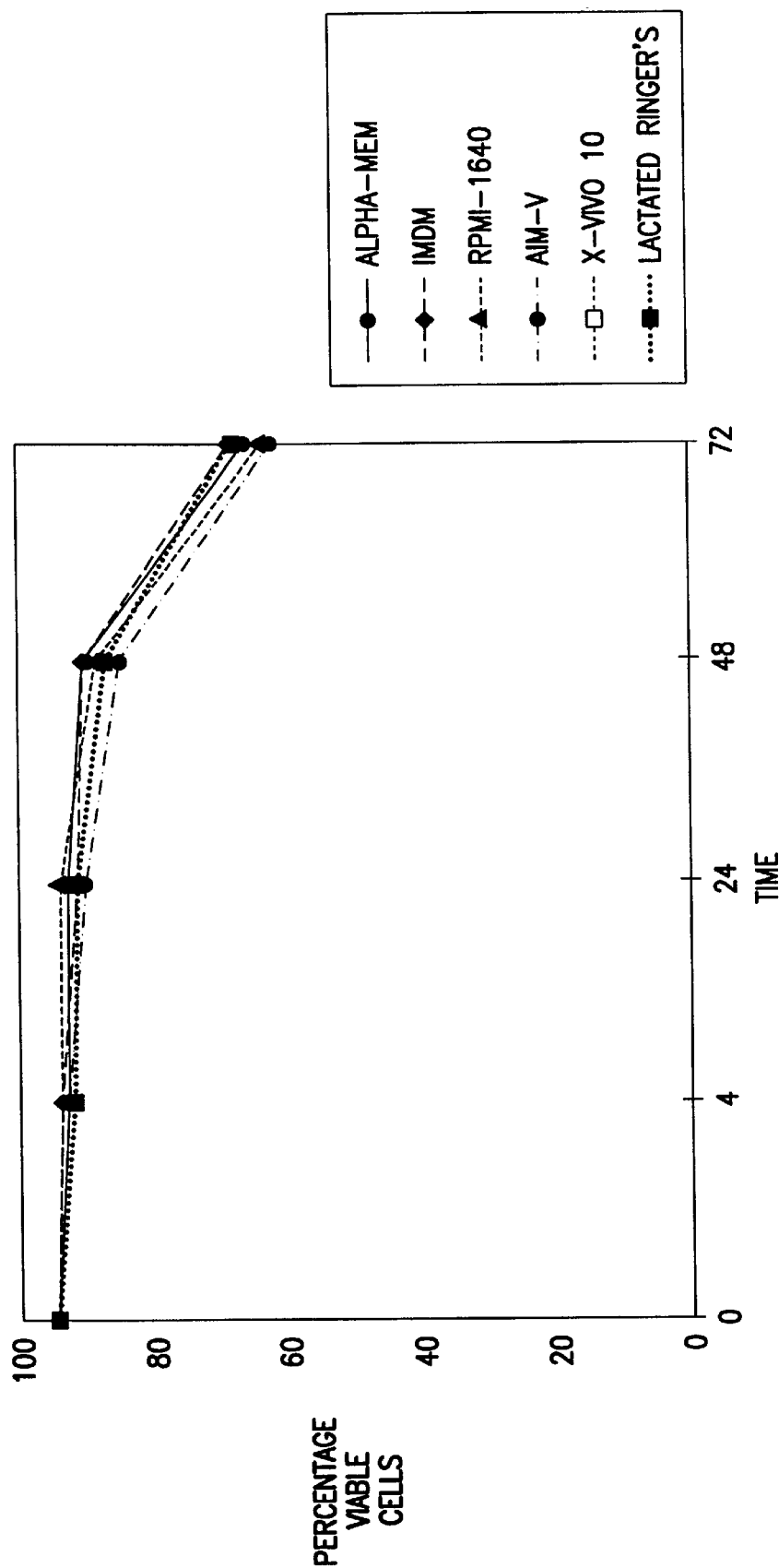
FIG. 2B shows the mean percentage, n=5, of viable nucleated cells in six media (5 tissue culture media and lactated Ringer's solution), maintained at 4° C., wherein $1\times10^6$ cells/ml of α-MEM, RPMI 1640, IMDM, AIM-V, X-VIVO and lactated Ringer's solution. All media contain about 1% HSA.

The terms "infusible" or "infusible-grade" refer to compounds, chemicals, solutions, compositions, mediums, agents, proteins or suspensions that are known to be safe, or have been determined to be safe for human use e.g., by injection or infusion, and have preferably been approved for human infusion or injection by a United States regulatory agency, e.g., the Food and Drug Administration ("FDA").

The term "electrolyte replenisher base solution" refers to a balanced salt solution primarily based on the physiological saline first developed by Ringer. These solutions are composed primarily of inorganic salts and can be supplemented with sugar. Typically, they contain no antimicrobial agents. Balanced salt solutions are used for fluid electrolyte replacement therapy, washing tissues and cells, and as diluents for treating cells and tissues with various agents, while maintaining a physiological pH and osmotic pressure. Examples of electrolyte replenisher base solutions of the present invention include lactated Ringer's solution, Hank's Balanced Salt Solution (free from phenol red), and those solutions sold under the trademarks of PLASMALYTE-A, NORMOSOL-R, VEEN-D, and POLYSAL.

The term "cell storage medium" or "storage medium" refers to a liquid medium (solution or suspension), capable of preserving cell viability, cell proliferative capabilities and metabolism of isolated cells against injury associated with the storage and transport of cells. The term further refers to a medium (solution or suspension) that contains components known to be safe for human infusion or injection. Preferably, the medium (solution or suspension), and components or elements of the medium are approved by a United States regulatory agency for infusion or injection into humans, e.g., the FDA.

The term "stem cell" or "hematopoietic stem cell" refers to a population of blood cells enriched in pluripotent cells which are uncommitted to a particular cell lineage and therefore retain the ability of self-renewal and the ability to differentiate into a specific lineage, such as "committed progenitor cells," i.e., lymphoid stem cells, which mature into B lymphocytes and T lymphocytes, or myeloid or erythroid stem cells, which mature into red blood cells, granulocytes, monocytes, and megakaryocytes. Alternatively, stem cells, nucleated cells and other hematopoietic cells, can be obtained directly from a patient or donor's blood forming tissues, e.g., peripheral blood, bone marrow or umbilical cord blood.

The term "mononuclear cells" refers to any cell found in blood or blood-forming tissues with a nucleus which is not segmented. These cells range from very primitive undifferentiated cells to mature cells, and include but are not limited to pluripotent stem cells, committed and uncommitted progenitor cells, lymphocytes and monocytes. Mononuclear cells can be obtained directly form a mammalian donor source or alternatively from a blood product source.

The term "nucleated cells" refers to cells that possess nuclei, e.g., white blood cells, and includes cells such as mononuclear cells, but does not include cells such as platelets or red blood cells.

The term "physiological pH" refers to a pH, which is the measure of the acidity or alkalinity of a solution or composition, that numerically encompasses a neutral range of about 6.9–7.5, and more preferably about 7.1–7.4.

The terms "tissue culture media components or "cell culture media components" refer to known components of tissue or cell culture media. Such media include RPMI 1640, IMDM, AIM-5, X-VfVO 10, α MEM and other known tissue culture and cell culture media known to the art. These media, in addition to the usual small molecules, usually contain one or more specific proteins that most cells require in order to survive and proliferate in culture. These include growth factors, that stimulate cell proliferation, and transferrin, which carries iron into cells. Several of these components are not safe for human injection or infusion, e.g., phenol red and constituents not available in U.S.P. grade.

The term "biological activity" refers to the viability or activity of stem cells and other hematopoietic cells removed from or contained within a cell suspension or cell storage medium of the present invention that have been stored and/or transported in a cell storage medium as compared to the viability or biological activity of stem cells that have not been stored and/or transported. Such viability or activity can be determined by assays such as those discussed hereinbelow. Cells having undergone a storage or transport event in a suspension of the present media have at least 20–40% viability or activity when compared to isolated non-stored/transported stem cells, preferably 41–55%, more preferably 56–70%, and most preferably 71–90% viability or biological activity.

The term "viability assay" or "biological activity assay" refers to an assay available to determine the viability or biological activity of stem cells and other hematopoietic cells, and the percentage recovery of viable or biologically active cells removed from or contained within a cell suspension or cell storage medium. Aliquots from samples can be tested via a (1) membrane integrity assay using fluorescent markers such as acridine orange ("AO") and propidium iodine ("PI"), (2) total cell count assay via a hemocytometer, (3) proliferative capability of the cells in a methylcellulose culture, (4) long-term culture-initiating cell assay (LTC-IC), or (5) flow cytometry to enumerate the percentage of $CD34^+$/$CD45^+$ cells. These assays are more fully described hereinbelow.

The term "cell suspension" refers to a population or concentration of nucleated cells, e.g., mononuclear cells, stem cells or other hematopoietic cells in a cell storage medium in a flowable or non-frozen state.

HSA can be obtained in a 25% weight/volume percent (w/v %) solution (Baxter, Hyland Division), and added to a medium of the instant invention in a volume/volume dilution (v/v %). ACDA, ACD and sodium citrate are used at a volume/volume percent (v/v %) in solution and can be measured in parts/ml. The anticoagulant heparin is used in a concentration of unit(s)/mi. All other percentages are by weight percent unless otherwise indicated.

Cell Storage Medium

The cell storage medium of the instant invention employs an electrolyte replenisher base solution selected from the group consisting of lactated Ringer's solution, Hank's Balanced Salt Solution (free from phenol red), and those solutions sold under the trademarks of PLASMALYTE-A, NORMOSOL-R, VEEN-D, and POLYSAL. These base solutions represent preferred base solutions as they closely approximate the composition of extracellular physiological fluids. Lactated Ringer's solution and PLASMALYTE-A non-polymeric expander, are representative of the most preferred electrolyte replenisher base solutions for use in the present invention.

Lactated Ringer's solution is a sterile solution of calcium chloride, potassium chloride, sodium chloride, and sodium lactate in water suitable for injection. Lactated Ringer's solution contains about 130 mEq/liter of sodium (Na), about 4 mEq/liter of potassium (K), about 109 mEq/liter of chloride (Cl), about 3 mEq/liter of calcium (Ca), about 28 mEq/liter of lactate, and about 5 mEq/liter of glucose. (Lactated Ringer's solution is commercially available from Baxter, Hyland Division, Glendale Calif., Product No. 2B2073).

PLASMALYTE-A is a non-polymeric plasma expander and contains essential salts and nutrients similar to those found in culture medium but does not contain additional constituents found in tissue culture medium which are not approved for human infusion, e.g. constituents not available in U.S.P. grade and phenol red. PLASMALYTE-A non-polymeric expander, contains about 140 mEq/liter of sodium (Na), about 5 mEq/liter of potassium (K), about 3 mEq/liter of magnesium (Mg), about 98 mEq/liter of chloride (Cl), about 27 mEq/liter of acetate, and about 23 mEq/liter of gluconate. PLASMALYTE-A non-polymeric expander, is commercially available from Baxter, Hyland Division, Glendale Calif., product No. 2B2543).

NORMOSOL-R is a sterile solution of magnesium chloride, potassium chloride, sodium chloride and sodium acetate, and also contains gluconate. NORMOSOL-R sterile solution contains about 140 mEq/liter of sodium (Na), 5 mEq/liter of potassium (K), 3 mEq/liter of magnesium (Mg), 98 mEq/liter of chloride (Cl), 23 mEq/liter of gluconate, and 5 mEq/liter of glucose. (NORMOSOL-R sterile solution is commercially available from Abbott Labs, Chicago Ill., product No. 796703).

VEEN-D is a sterile solution of calcium chloride, potassium chloride, sodium chloride, and sodium acetate, and contains about 130 mEq/liter of sodium (Na), about 4 mEq/liter of potassium (K), about 109 mEq/liter of chloride (Cl), about 3 mEq/liter of calcium (Ca), about 27 grams/liter of acetate, and about 5 mEq/liter of glucose.

POLYSAL is a minimum essential tissue culture medium ("MEM") that is a balanced polyionic electrolyte solution and contains about 140 mEq/liter of sodium, about 103 mEq/liter of chloride, about 5 mg/deciliter of calcium, about 3 mg/deciliter of magnesium, and about 55 mEq/liter of acetate maintained at a physiological pH. (POLYSAL minimum essential tissue culture medium is commercially available from Cutter Biologicals, Emeryville Calif.).

Hank's Balanced Salt Solution (containing no phenol red) ("HBSS"), contains inorganic salts such as potassium chloride (KCl), about 4 g/liter; potassium phosphate monobasic ($KH_2PO_4$), about 600 mg/liter; sodium chloride (NaCl), about 80 g/liter; sodium phosphate dibasic ($Na_2HPO4$), about 475 mg/liter; and glucose, about 10 g/liter. HBSS is buffered with phosphate so that the solution will maintain its physiological pH under atmospheric conditions. For this reason it is the primary solution used in enzymatic treatments of cells and tissue and the final rinse of cells prior to the suspension of the cells in a complete growth medium. (HBSS is commercially available from Sigma Chemical Co., product H-1387).

Anticoagulants are substances or drugs which delay coagulation of blood and are of three general types: (1) calcium sequestering agents, (2) heparin and heparin substitutes, and (3) prothrombopenic anticoagulants. Preferred anticoagulants of the instant invention include heparin (Fujisawa, Deerfield, Ill.), ACDA (Baxter, Deerfield, Ill.), ACD (Baxter, Deerfield Ill.) and sodium citrate (Baxter, Deerfield, Ill.).

The cell storage medium of the present invention may employ an anticoagulant either directly in a cell storage medium or in a wash step of cells prior to suspension in a storage medium. Typically, heparin is utilized at a concentration of about 1–75 units/ml of storage medium. ACD, ACDA or sodium citrate can be utilized in a concentration of about 1.0–10 parts/ml of storage medium.

A method of washing cells, can be employed, for example, by adding heparin to 1X PBS to yield a final concentration of about 20 units heparin/mil of medium. A sample can then be diluted 1:1 with the prepared heparinized PBS. For example, for a 50 ml sample, 50 ml of heparinized PBS would be added to yield a total volume of 100 ml. The sample can then be centrifuged at approximately 300 g for 5 minutes, however, higher g-forces and longer centrifugation times can be employed. The supernatant is removed and the washed cells are resuspended in a cell storage medium at a desired concentration.

The present storage medium also employs human serum albumin ("HSA"). HSA is a sterile, non-pyrogenic preparation of serum albumin that can be obtained by fractionating blood, plasma, serum or placentas from healthy human donors. The albumin content is not less than 96% of the total protein. HSA may contain sodium acetytryptophanate alone, or with sodium caprylate as a stabilizing agent. The sodium content is not less than 130 mEq/liter and not more that 160 mEq/liter and contains no microbial agents. HSA is used in a cell storage medium of the present invention in a concentration of about 0.1–10%, preferably about 0.25%–7.5%, and most preferably about 1–5%.

Histidine Buffering

A cell storage medium containing an electrolyte replenisher base solution as set forth above is preferably buffered by a buffering agent that has been approved for in vivo use in humans. In the instant application, the buffering agent histidine is preferably used. In the present invention, histidine is present in an amount effective to maintain a cell storage medium, solution, composition or cell suspension at physiological pH. Histidine is used in a concentration of about 10 mM–100 mM, more preferably about 25 mM to 75 mM, and most preferably about 50 mM in a cell storage medium.

In a storage medium of the instant invention, histidine effectively provides a high degree of pH control of a cell suspension independent of the storage container utilized or the storage temperature, e.g., 4° C. or room-temperature (20°–24° C.). Although maintenance of a stable pH is important for infusion purposes, in a comparison between a histidine buffered medium containing lactated Ringer's solution and non-buffered medium containing lactated Ringer's solution, there was no significant difference noted in several of the biological activity parameters measured, e.g., cell membrane integrity and cell proliferative capability. Although buffered and non-buffered media were not compared side by side in the same series of experiments, these results suggest a non-buffered medium containing lactated Ringer's solution having about 1% HSA may provide a sufficiently hospitable storage environment for hematopoietic stem cells. However, it is believed this may not be the case when cells are stored at higher concentrations, e.g., approximating cell concentrations encountered in clinical laboratories. Example 2 demonstrates the effectiveness of histidine in buffering a cell storage medium of the instant invention.

The results, as shown in Example 2, indicate that a cell storage medium buffered by 50 mM histidine based on either PLASMALYTE-A non-polymeric expander, or lactated Ringer's solution can function as infusible-grade short-term cell storage medium, although a medium based on lactated Ringer's solution was slightly superior with regard to the preservation of viable mononuclear cells and maintenance of functional progenitor cells. Additionally, although both solutions performed satisfactorily in all three bags tested, the most favorable storage conditions were observed for a medium containing lactated Ringer's solution buffered with 50 mM histidine and maintained at 4° C.

Moreover, a 50 mM histidine buffered infusible-grade storage medium containing lactated Ringer's solution typically equaled or exceeded the performance of currently-used culture media in a variety of assays of cell viability, function, and phenotype. Even in those instances where a storage medium containing lactated Ringer's solution was not clearly superior to conventional tissue culture media, it rarely performed below the average for culture media containing solutions.

Hematopoietic Stem

Hematopoietic stem cells can be obtained in accord with the present invention from patients or normal human donors stimulated with granulocyte-colony stimulating factor ("G-CSF") or other chemotherapeutic agents. Donors can be administered G-CSF, for example 5–12 $\mu$g/kg for a period of 1–6 days, and an apheresis product can then be collected. Generally, an apheresis product is purified and rich in mononuclear cells, but if additional cell purification or processing is desired, density gradient separation techniques and centrifugation techniques as set forth in the specification, and techniques known in the art can be implemented.

Alternatively, stem cells, nucleated cells and other hematopoietic cells can be obtained from other methods employing positive and negative selection techniques. For example, cells can be obtained from mammalian bone marrow, as from human bone marrow, e.g., by centrifugation and the immunomagnetic and FACS procedures as described in C. Verfaillie et al., *J. Exp. Med.*, 172:509 (1990). This procedure yields cell populations highly-enriched in human stem cells which are characterized by being Lin⁻ CD34⁺ DR⁻. Other hematopoietic cell populations having enriched stem cells include the CD34⁺ population disclosed by Civin (U.S. Pat. No. 4,714,680), the CD34⁺, CD38⁻ population disclosed in European patent application No. 455,482, and the population disclosed by Tsukamato et al. (U.S. Pat. No. 5,061,620). See also, Champlin R., *J. Hematotherapy* 4:53–60 (1995); Noga S J., *J. Hematotherapy* 1:3–17 (1992); Preti et al., *J. Hematotherapy* 2:103–109 (1993); *Bone Marrow and Stem Cell Processing: A Manual of Current Techniques*, edited by Areman et al., F. A. Davis Company (1992). Upon the isolation and purification of cells, the cells can be added or suspended in the cell storage medium of the instant invention.

In the present invention, the final cell concentration in a cell storage medium should not exceed $5\times10^8$ cells per ml of medium. Cell concentration can be determined by means of a COULTER cell counter or hemocytometer. Additionally, in order to minimize the load on the cardiovascular and renal systems, it is desirable to reduce the overall volume of medium infused into a human patient, which requires maximizing the cell concentration used. Thus, stem cell suspensions are prepared in accordance with the present invention by providing a population of isolated and purified hematopoietic stem cells and introducing them into a cell storage medium. In the present invention, the cell concentration can average about $1\times10^4$–$5.0\times10^8$ cells/ml of medium, preferably about $1\times10^6$–$1\times10^8$ cells/ml of medium, and most preferably about $1\times10^7$–$5.0\times10^7$ cells/ml of medium.

Measuring Biological Activity

In a preferred embodiment of the invention, a variety of in vitro assays can be performed in order to assess cell morphology, phenotype, viability and functional capability in a cell storage medium of the present invention. Assays include those set forth in Table 1, and as described below.

TABLE 1

Cell assay methods for a cell storage medium.

| Parameter Studied | Method | Use |
|---|---|---|
| Cell number, morphology | Automated WBC, manual differential | Calculate yield or degree of cell loss of mononuclear cells for each solution, under each condition. |
| Cell viability | Acridine orange-propidium iodide dual-staining detected by fluorescence microscopy | Determine the number or proportion of cells that are living for each solution, under each condition. |
| Cell function | Progenitor assay (enumerate CFU-GM, BFU-E) | Determine the degree to which different solutions affect the ability of cells to produce tri-lineage hematopoiesis. |
| Stem or near-stem cell function | Long-term culture-initiating cell (LTC-IC) assay | Detect and enumerate extremely primitive hematopoietic stem cells. |
| Cell surface phenotype | Flow cytometry to enumerate percentage of CD34⁺ or CD34⁺/CD45⁺ cells | Determine the degree of preservation of cells having the surface phenotype of stem and progenitor cells. |
| Solution pH | Automated measurement | Determine whether pH remains within a range compatible with long-term cell survival. |

In the present invention, cells tested were peripheral blood mononuclear cells obtained by cytapheresis of a G-CSF-stimulated normal human donor, as are now used in allogeneic peripheral blood stem cell transplantation (Stroncek et al., *Transfusion* 36:601–610 (1996); Anderlini et al., *Transfusion* 31:590–595 (1996)). In initial experiments, cells were tested at a concentration of about $1\times10^6$ cells/ml of medium. In subsequent experiments, involving fewer variables, higher cell concentrations of $5\times10^6$, $1\times10^7$, $5.0\times10^7$, $1.0\times10^8$ and $5.0\times10^8$ cells/ml of medium were examined. Two temperatures, 4° C. and room temperature (approximately 20°–24° C.), and three types of gas-permeable bags, e.g., CRYOCYTE, PL3014 and PL2410 were used for storing cells in a storage medium. In order to conserve cells needed for studies, bags were reduced in size to 6×9 cm. Each bag was filled with approximately 15 ml of a cell suspension at the beginning of each study.

Cells were maintained in test solutions for up to 72 hours. Samples were taken at 0 hours, 4 hours, 24 hours, 48 hours and 72 hours. Data from the t=0 time point provided a baseline for comparison, while the t=4 hours time point provided a measure of the initial toxicity of a cell storage medium. The 24- and 48-hour time points represented an approximation of transport and storage times typically required in present-day clinical practice, while the 72-hour time point provides extreme environmental stress.

A cell suspension of the present invention can be prepared using a syringe, or other suitable means, to ensure even distribution of cells in the storage medium. Aliquots from a cell suspension can be removed and assayed to determine cell number and morphologic phenotype, from cell counts and differentials can be performed using a Coulter STKR-S automated cell counter (Read et al., *J. Hematotherapy* 30:812–816 (1992)).

Cell viability can be determined by measuring membrane integrity in the presence of two fluorescent dyes, acridine orange, (AO), and propidium iodide, (PI) (Bank, Diabetologia 30:812–816 (1987); Bank, *In vitro Cell. and Develop. Biol.* 24:266–273 (1988)). To determine membrane integrity using AO/PI, 5 μl of a cell suspension from a cell storage medium were diluted with 95 μl of IMDM. Equal amounts of cell suspension and AO/PI solution were added, the suspension was placed on the hemocytometer and cells were counted using fluorescent microscopy (Zeiss Axioskop, Germany). Cells which fluoresced green were considered viable, wherein cells that fluoresced red/orange were considered dead. By determining the total number of cells within a given region of the hemocytometer, it was possible to determine a cell concentration which, when multiplied by total volume, resulted in a total cell number in a suspension.

The percentage of initial viable mononuclear cells was calculated based on the nucleated cell count, differential and percentage of viable mononuclear cells. Mononuclear cells were defined as lymphocytes plus monocytes by differential. The t=0 nucleated cell count, volume, mononuclear cell percentage, and percent viable cells were used to calculate the total initial viable mononuclear cells, as follows:

Initial viable mononuclear cells=(total nucleated cells)×(% mononuclear cells)×(% viability)

Viable mononuclear cell number was similarly calculated for each subsequent time point, and compared with the t=0 value to generate the percentage of initial viable mononuclear cells, as follows:

$$\% \text{ of initial viable mononuclear cells} = 100 \times \frac{\text{viable mononuclear cells at time point}}{\text{initial viable mononuclear cells}}$$

The percentage of initial viable mononuclear cells was used to assess the degree of preservation of viable mononuclear cells, the morphologic type containing stem and progenitor cells, relative to their number at the beginning of the storage period.

Progenitor cell function was evaluated by growth for 14 days in recombinant cytokine-supplemented methylcellulose-based semisolid medium, (Stem Cell Technologies METHOCULT GF H4434) followed by enumeration and identification of colonies as myeloid (CFU-GM), eiythroid (BFU-E) or mixed (CFU-GEMM). All cultures were carried out in duplicate, at plating concentrations of both $2.5 \times 10^4$ and $5.0 \times 10^4$ cells/plate. This assay tested the most essential function of cells intended for transplantation, e.g., the ability to proliferate and differentiate (Gordon, *Blood Reviews* 7:190–197 (1993); Rowley et al., *Blood* 7:271–275 (1987)). This assay, due to its reliance on cell growth, has an inherent level of variability. Rather than over-interpret very small changes in the number of progenitors, the assay was used to determine whether progenitor cell function was preserved or adversely affected during storage.

Aliquots of cell suspensions, as set forth in Examples 1 and 2, were centrifuged at 500×g for about 2 minutes and the supernatant was removed. The pellet was resuspended in IMDM (Gibco, Grand Island, N.Y.) to a final concentration of $2 \times 10^6$ viable cells/ml. Subsequently, $2 \times 10^4$ and $5 \times 10^4$ cells were added to 1 ml of METHOCULT recombinant cytokine-supplemented methylcellulose culture medium for stem cells. The mixture was supplemented with IMDM+2% fetal calf serum (Gibco, Grand Island, N.Y.), mixed and pipetted into 35×10 mm petri dishes (Falcon, Plymouth, England). The cultures were then placed in a misted air incubator for 2 weeks and colony formation was determined. Colonies were scored for CFU-GM, CFU-GEMM and BFU-E and the total number of colonies were counted.

A Long-Term Culture-Initiating Cell (LTC-IC) assay is employed to detect cells capable of self-renewal as well as proliferation and differentiation. Self-renewing cells represent the stem and near-stem cell population critical for long-term survival in transplantation. An LTC-IC assay involves a five-week liquid culture in the presence of an irradiated stromal cell monolayer during which progenitor cells incapable of self-renewal are lost. The remaining, self-renewing cells are detected using a standard 14-day progenitor assay as described above.

Cell surface immunologic phenotype was determined by flow cytometry using fluorescent-conjugated monoclonal antibodies specific for CD34, e.g., phycoerythrin conjugate (Becton-Dickinson) and CD45, e.g., fluorescein isothiocyanate conjugate (Becton-Dickinson). Cells were analyzed on a Becton-Dickinson FACScan, using the methods of Sutherland et al., *Expt. Hematology* 22: 1003–1010 (1994); Bender et al., *Hematotherapy* 2:421–430 (1993)). This assay permitted accurate quantitation of $CD34^+/CD45^+$ cells to the degree feasible with current flow cytometry technology. However, due to some inherent variability in the $CD34^+/CD45^+$ cell measurements, observed differences in $CD34^+/CD45^+$ percentages are not believed to be significant. The purpose of this assay, like the progenitor assay, is to determine whether a stem and progenitor cell population are adversely affected in a cell storage medium.

As stated previously, experiments evaluating the instant invention have been performed using G-CSF-stimulated peripheral blood stem cells. This is appropriate, in that this source of hematopoietic cells is rapidly becoming predominant in transplantation. Bone marrow, however, continues to be the graft type most commonly transported between centers and thus has the greatest requirement for a cell storage medium. Umbilical cord blood represents another source of transplantable hematopoietic cells that would benefit from an effective infusible-grade cell storage medium. Other cells, such as lymphocytes, natural killer cells and other cells used in adoptive immunotherapy could also benefit from the storage medium of the instant invention.

A cell storage medium buffered with 50 mM histidine containing hematopoietic stem cells and supplemented with HSA has been prepared and successfully used in the method of this invention. This storage medium maintains the biological activity of stem cells following suspension into the medium and storage for at least a 72 hour time period, are described in the following Examples.

EXAMPLE 1

Formulation of a Cell Storage Medium

Stem cells were collected from an apheresis product obtained from normal donors stimulated with G-CSF. Donors were given G-CSF (10 μg/kg for 4 days) and the apheresis product was collected on day 5. The apheresis product was centrifuged at 300×g for about 5 minutes, the plasma supernatant was removed, and the cell pellet was resuspended in 50 ml of a cell storage medium as described below.

A comparison of tissue culture media and a medium of the present invention was made. Cells were suspended in test media at a concentration of approximately $1-5 \times 10^6$ cells/ml in α-MEM, RPMI 1640, IMDM, AIM-V, X-VIVO-10 and lactated Ringer's solution. All media were supplemented with HSA at concentrations of about 1% and about 10%. Fifteen ml of each cell suspension were stored in CRYO-CYTE bags (Baxter, Fenwal Division, Deerfield, Ill.). Percent viable cells via a membrane integrity assay were determined for each prepared medium at room-temperature and 4° C. at 0, 4, 24, 48 and 72 hour time points. (FIGS. 1A, 1B, 2A and 2B). Table 2 below summarizes the percent cell viability as determined by a membrane integrity assay for cells taken from each tested medium at the 72 hour time point.

TABLE 2

| Cell Storage Medium | % Viability @ 72 hrs 20–24° C. | % Viability @ 72 hrs 4° C. |
| --- | --- | --- |
| α-MEM + 10% HSA | 34.2 ± 26.2 | 48.5 ± 7.9 |
| α-MEM + 1% HSA | 60.2 ± 11.5 | 65.7 ± 10.8 |
| RPMI 1640 + 10% HSA | 43.6 ± 31.7 | 50.9 ± 5.3 |
| RPMI 1640 + 1% HSA | 43.4 ± 27.1 | 62.8 ± 17.1 |
| IMDM + 10% HSA | 35.0 ± 28.1 | 43.4 ± 12.3 |
| IMDM + 1% HSA | 58.0 ± 5.0 | 68.3 ± 14.9 |
| AIM-V + 10% HSA | 28.1 ± 0.3 | 43.3 ± 4.9 |
| AIM-V + 1% HSA | 47.5 ± 22.5 | 61.8 ± 18.5 |
| X-VIVO + 10% HSA | 20.9 ± 10.3 | 61.4 ± 0.4 |
| X-VIVO + 1% HSA | 43.0 ± 18.2 | 67.5 ± 4.7 |
| lactated Ringer's solution + 10% HSA | 61.7 ± 13.9 | 68.3 ± 10.3 |
| lactated Ringer's solution + 1% HSA | 68.7 ± 4.8 | 67.1 ± 11.5 |

As shown in Table 2, a cell storage medium containing a base solution containing lactated Ringer's solution, maintained cell viability better than a medium containing cell culture media at room temperature, e.g., 70±3% (20°–24° C.), and better than most of the culture medias at 4° C., e.g., 67±3%.

The percentage of $CD34^+/CD45^+$ cells measured in a medium containing lactated Ringer's solution was similar to or exceeded the levels observed for other solutions, e.g., 1.4±3% at room temperature and 3.6±3% at 4° C. The mean number of CFU-GM per $10^4$ mononuclear cells plated, measured at t=0, 24 and 48 hours were also determined. At room-temperature storage (20°–24° C.), a medium containing lactated Ringer's solution exhibited average preservation of CFU-GM until 48 hours. At 4° C., however, the medium containing lactated Ringer's solution maintained progenitor cell function extremely well, e.g., 16 CFU-GM, exceeded only by a medium containing AIM-V at the 24 hour point, e.g., 26 CFU-GM.

For the erythroid progenitor function, mean measured as BFU-E per $10^4$ mononuclear cells plated, at t=0, 24 and 48 hours, a medium containing a base of lactated Ringer's solution was more effective at 4° C. than room temperature, e.g., 21 BFU-E at 24 hours and 12 BFU-E at 24 hours respectively. At either temperature, however, a medium containing lactated Ringer's solution effectively maintained erythroid progenitors when compared with the non-infusible grade culture media, as the effectiveness of a medium containing lactated Ringer's solution at 4° C. was exceeded only by that of a medium containing AIM-V at the 24 hour time point, e.g., 21 BFU-E and 32 BFU-E respectively.

The mean pH for this experiment showed that a medium containing a base of lactated Ringer's solution and no buffering system, maintained a relatively stable solution pH for 24 hours at room-temperature and at 4° C. After 48 hours, the pH dropped to 6.70 at room temperature and increased to 7.08 at 4° C. As five of the tissue culture media solutions tested contained phosphate-based buffering systems that are ineffective at atmospheric $CO_2$ concentrations, the pH rose rapidly, ranging from 7.40 to 7.80 by 24 hours at room temperature, and from 7.50 to 7.65 by 24 hours at 4° C.

EXAMPLE 2

Histidine Buffering of a Cell Storage Medium

To measure the effectiveness of histidine buffering of a cell storage medium of the instant invention, 4 storage mediums were prepared. Two storage mediums contained lactated Ringer's solution supplemented with about 1% HSA and 50 mM histidine, and two storage mediums contained PLASMALYTE-A non-polymeric expander, supplemented with about 1% HSA and 50 mM histidine. All 4 media were mixed with cells to a concentration of $1 \times 10^6$ cells/ml of storage medium to yield a cell suspension. Fifteen ml of the resulting suspensions were then stored in CRYOCYTE, PL2410 and PL3014 bags at room-temperature (20°–24°) and 4° C. One ml aliquots were removed and assayed for cell viability at 0, 4, 24, 48 and 72 hours.

A measurement of the mean pH of each medium indicated that histidine buffering was extremely effective when used with a storage medium containing either PLASMALYTE-A non-polymeric expander, or lactated Ringer's solution, as pH was maintained for the entire 72 hour test period at approximately 7.13 for all four solutions, whether at room-temperature (20°–24° C.) or 4° C. and in all storage bags. A pH change observed after 72 hours with a cell storage medium containing a lactated Ringer's solution and no histidine, to approximately 6.70, did not occur in the presence of 50 mM histidine buffer.

Figure 3A:
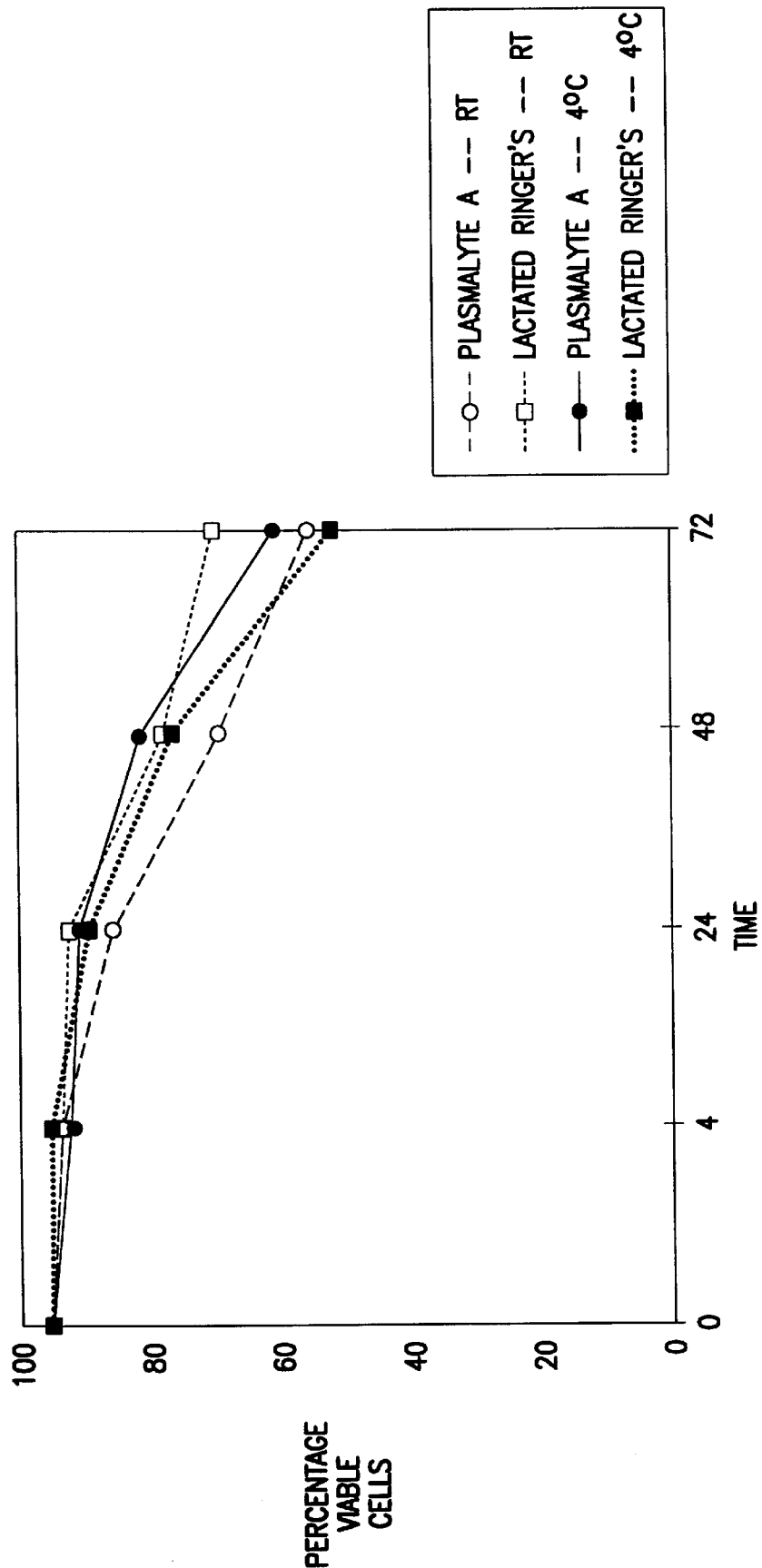
FIG. 3A shows the mean percentage, n=5, of viable nucleated cells suspended in a concentration of $1\times10^6$ cells/ml lactated Ringer's solution and PLASMALYTE-A non-polymeric expander, buffered with 50 mM histidine and supplemented with about 1% HSA stored in CRYOCYTE bags over a 72 hour time period and maintained at 4° C. and room-temperature (20°–24° C.).
Figure 3B:
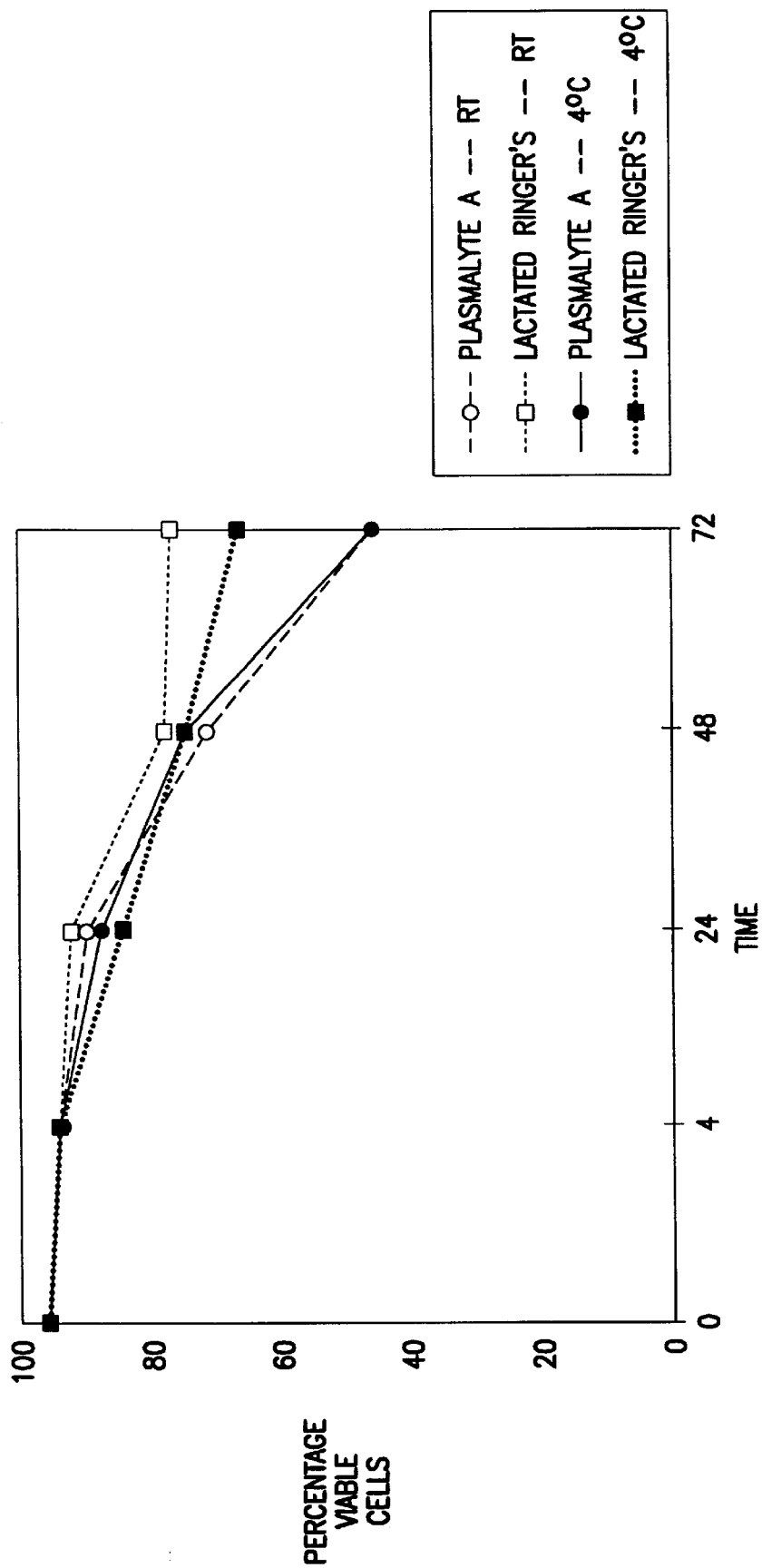
FIG. 3B shows the mean percentage, n=5, of viable nucleated cells suspended in a concentration of $1\times10^6$ cells/ml lactated Ringer's solution and PLASMALYTE-A non-polymeric expander, buffered with 50 mM histidine and supplemented with about 1% HSA stored in PL2410 bags over a 72 hour time period and maintained at 4° C. and room-temperature (20°–24° C.).
Figure 3C:
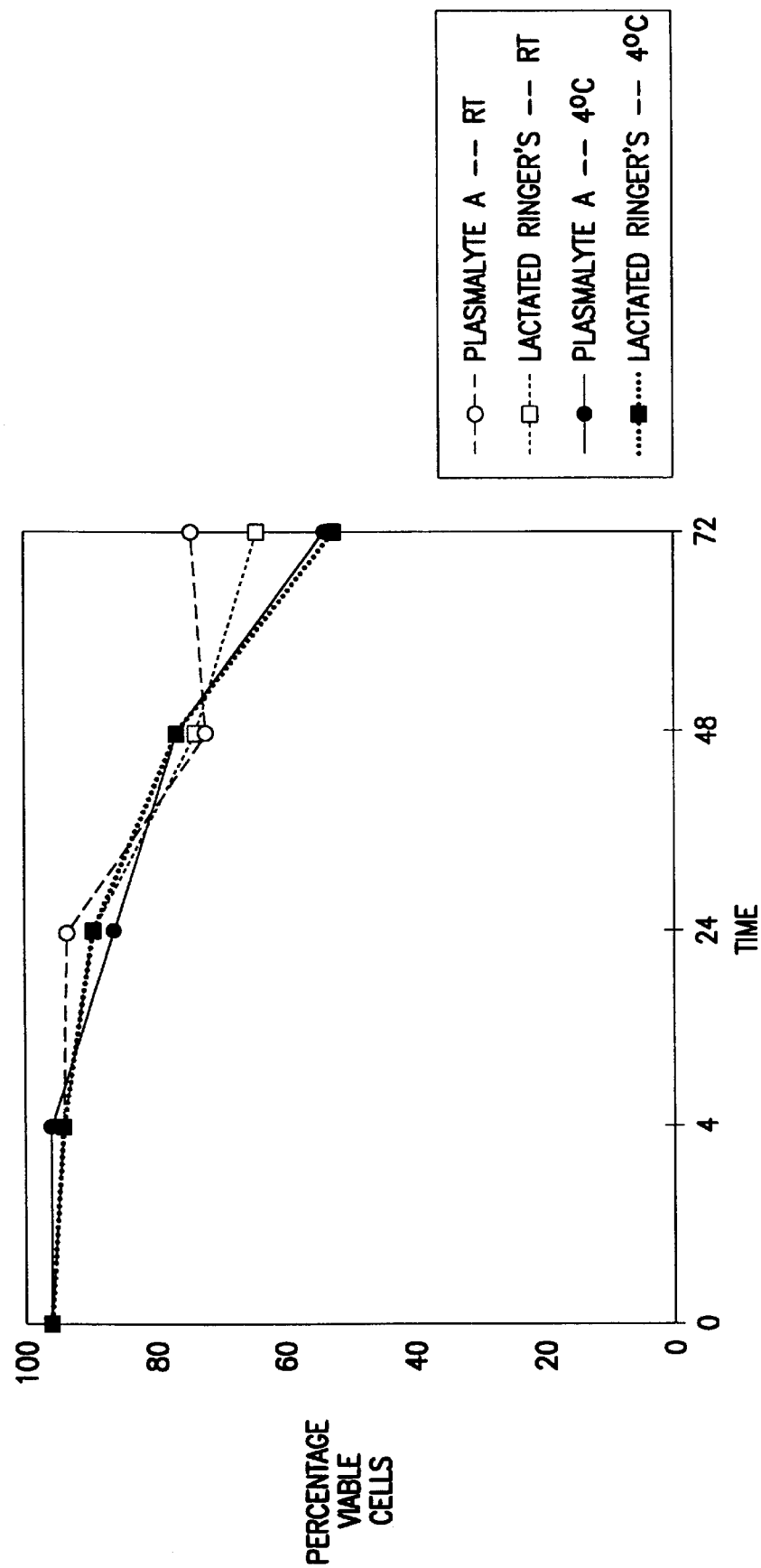
FIG. 3C shows the mean percentage, n=5, of viable nucleated cells suspended in a concentration of $1\times10^6$ cells/ml lactated Ringer's solution and PLASMALYTE-A non-polymeric expander, buffered with 50 mM histidine and supplemented with about 1% HSA stored in PL3014 bags over a 72 hour time period and maintained at 4° C. and room-temperature (20°–24° C.).

FIGS. 3A, 3D and 3C show the mean percentage of viable cells at 0, 4, 24, 48 and 72 hour time points as determined by a membrane integrity assay using AO and PI fluorescent markers. All four prepared storage media maintained at 4° C. or room-temperature reflected a percent viability of about 50 to 80% for cells assayed.

A total cell count showed cells stored in a storage medium containing lactated Ringer's solution at 4° C. gave superior results as indicated by the mean percentage of initial viable mononuclear cells remaining at each time point, e.g., about 90–95% at 24 hrs, about 82–85% at 48 hrs and about 50–70% at 72 hrs.

Figure 5A:
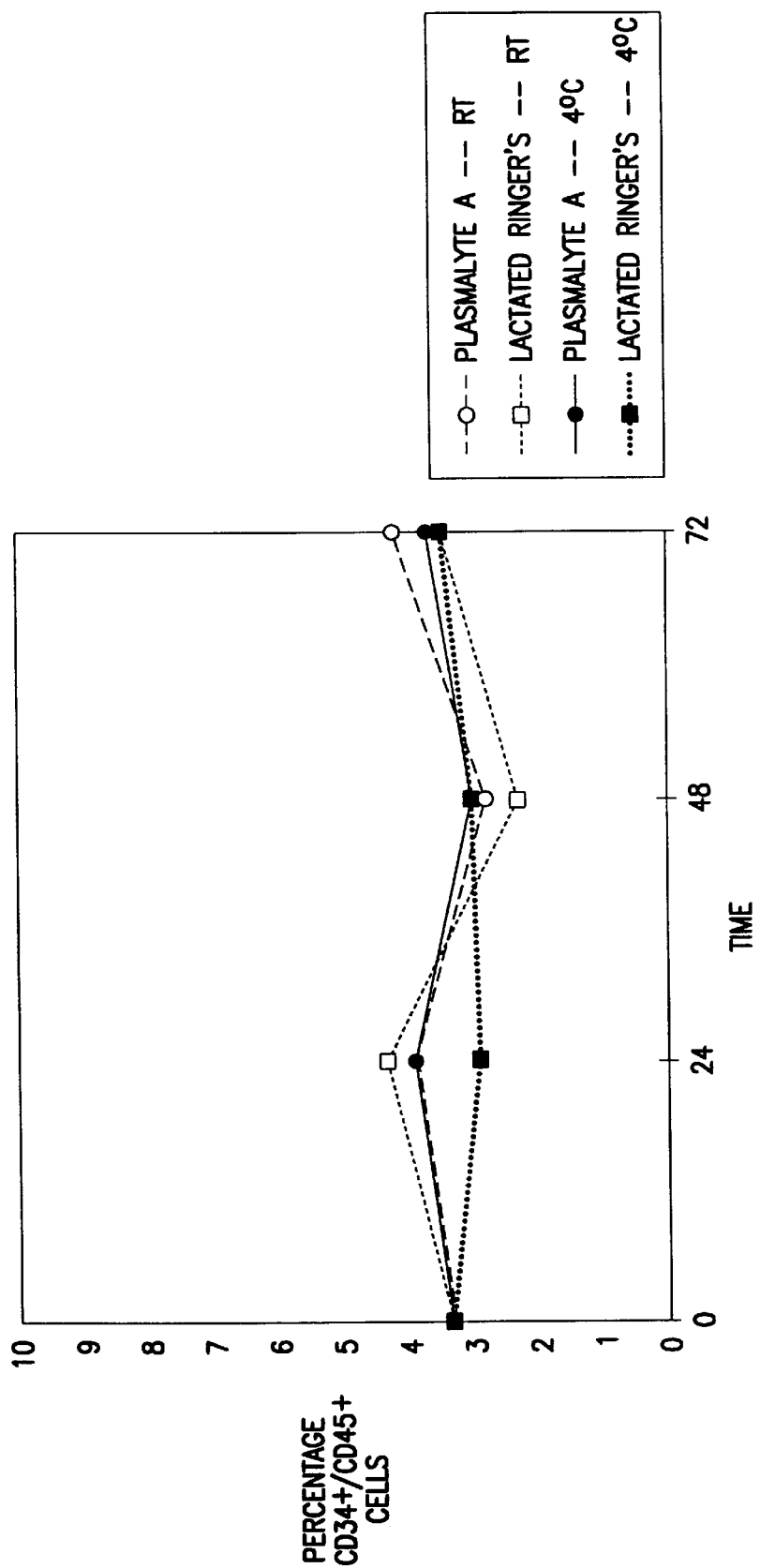
FIG. 5A shows the mean percentage, n=5, of $CD34^+$/$CD45^+$ cells suspended in a concentration of about $1 \times 10^6$ cells/ml of lactated Ringer's solution and PLASMALYTE-A non-polymeric expander, buffered with 50 mM histidine and supplemented with about 1% HSA stored in PL2410 bags over a 72 hour time period and maintained at 4° C. and room temperature (20°–24° C.).

In a flow cytometry assay, the mean percentage of $CD34^+/CD45^+$ cells at each time point was not higher in either a storage medium containing lactated Ringer's solution or PLASMALYTE-A non-polymeric expander. The percentage of CD34+/CD45+ cells as determined by flow cytometry for either medium was about 3 to 4% through the 72 hr timepoint (FIG. 5A).

To determine proliferative capability of stem cells, an aliquot of a cell suspension from each of the 4 prepared storage media were centrifuged at 500×g for 2 minutes and the supernatant was removed. The pellet was resuspended in IMDM to a final concentration of 2×10$^6$ viable cells/ml. Subsequently, 2.5×10$^4$ or 5.0×10 cells were added to 1 ml of METHOCULT methylcellulose culture medium for stem cells. The mixture was supplemented with IMDM+2% fetal calf serum (Gibco, Grand Island, N.Y.), mixed and pipetted into 35×10 mm petri dishes (Falcon, Plymouth, England). The cultures were then placed in a misted air incubator for 2 weeks and colony formation was determined. Colonies were scored for CFU-GM, CFU-GEMM and BFU-E and the total number of colonies were counted. Cell suspensions stored in a medium containing lactated Ringer's solution preserved CFU-GM slightly better than a medium containing PLASMALYTE-A non-polymeric expander, particularly in PL2410 and PL3014 bags. The mean number of BFU-E per 10$^4$ mononuclear cells plated was similar in a medium containing lactated Ringer's solution or PLASMALYTE-A non-polymeric expander, or storage at 4° C. or room-temperature.

Surprisingly, in a medium of the instant invention the viability of neutrophils/granulocytes was sustained, e.g., remained constant, over a 72 hour time period as shown in Table 3. Additionally, at 4° C., neutrophil/granulocyte viability was sustained for about 48 hours.

TABLE 3

| HOUR | MEDIUM | TEMP | TOTAL VIABLE NEUTROPHILS (cells × 10$^6$/ml) | |
|---|---|---|---|---|
| | | | mean | sd |
| 0 | lactated Ringer's soln. + 1% HSA + 50 mM histidine | 20–24° C. | 0.53 | 0.10 |
| 0 | lactated Ringer's soln. + 1% HSA + 50 mM histidine | 4° C. | 1.29 | 0.69 |
| 4 | lactated Ringer's soln. + 1% HSA + 50 mM histidine | 20–24° C. | 0.49 | 0.33 |
| 4 | lactated Ringer's soln. + 1% HSA + 50 mM histidine | 4° C. | 0.79 | 0.33 |
| 24 | lactated Ringer's soln. + 1% HSA + 50 mM histidine | 20–24° C. | 0.59 | 0.14 |
| 24 | lactated Ringer's sonl. + 1% HSA + 50 mM histidine | 4° C. | 0.41 | 0.20 |
| 48 | lactated Ringer's soln. + 1% HSA + 50 mM histidine | 20–24° C. | 0.34 | 0.28 |
| 48 | lactated Ringer's soln. + 1% HSA + 50 mM histidine | 4° C. | 0.32 | 0.11 |
| 72 | lactated Ringer's soln. + 1% HSA + 50 mM histidine | 20–24° C. | 0.52 | 0.06 |
| 72 | lactated Ringer's soln. + 1% HSA + 50 mM histidine | 4° C. | 0.22 | 0.09 |

EXAMPLE 3

Storage of Cells at Varying Cell Concentrations With an Anticoagulant

Using cell concentrations of about 1–2×10$^8$ cells/ml of medium, cell viability as a function of time was determined for three (3) samples in three (3) different cell storage mediums. Each prepared cell storage medium contained lactated Ringer's solution+about 1% HSA+50 mM Histidine. As shown in Table 4, medium 1, contained no anticoagulant, medium 2 was supplemented with 20 units/ml of heparin, and medium 3 was supplemented with 0.38 g/L (0.38%) sodium citrate. Peripheral blood stem cells were utilized and obtained from a normal donor stimulated with G-CSF as set forth in Example 1. Viability as a function of time for the cells suspended in media containing an anticoagulant was determined.

TABLE 4

| | Medium # | | |
|---|---|---|---|
| | 1 | 2 | 3 |
| Time (hr) | Viability in medium without anticoagulant | Viability in medium with Heparin (20 units/ml) | Viability in medium with 0.38% sodium citrate |
| 0 | 97.5 ± 2.1 | 97.1 ± 1.6 | 94.6 ± 2 |
| 24 | 89.6 ± 7 | 90.8 ± 6.3 | 89.6 ± 3 |
| 48 | 70.8 ± 9 | 68.5 ± 12.2 | 65.6 ± 9 |

Table 4 shows the viability of mononuclear cells obtained from apheresis of normal solution mobilized with G-CSF as a function of time for a cell storage medium with or without an anticoagulant. All samples were washed with a heparinized PBS solution, as described above, prior to suspension in the medium of interest. The results showed the viability of cells suspended in a medium supplemented with an anticoagulant was comparable to that obtained in a medium absent an anticoagulant.

Samples from the three prepared mediums were removed and cultured in methylcellulose to determine the proliferative capability of the progenitor cells. There was no significant decrease in the total number of colonies observed over the 48 hours storage period for a medium supplemented with or without an anticoagulant.

The cells described in this experiment represent minimally manipulated cells, e.g., (washed only). Thus, platelets and clotting factors present in the original product are still present in high enough quantities to form clots. In addition to the observation of cell viability, pH and colony formation, visual observations indicate that for these minimally manipulated samples, the presence of anticoagulants inhibited clot formation in the samples. For samples in which anticoagulants were not present, persistent clots formed in the samples.

The pH of each medium remained between 6.9 to 7.2 for the entire duration of the experiment for all of the treatments e.g., with or without heparin/citrate. The results indicate that the addition of anticoagulants to a storage medium did not adversely effect the ability of 50 mM histidine to buffer the medium for the cell concentrations tested.

In a subsequent experiment utilizing cell concentrations approximating those observed in clinical laboratory applications, 5 hematopoietic stem cell suspensions were prepared in concentrations of 5.0×10$^6$, 1.0×10$^7$, 5.0×10$^7$, 1.0×10$^8$ and 5.0×10$^8$ cells/ml of a storage medium containing lactated Ringer's solution, about 1% HSA buffered with 50 mM histidine. As significant volumes of plasma accompany higher cell concentrations, all cells were washed with a heparinized phosphate-buffered saline (1X PBS) prior to suspension in a storage medium to prevent activation of coagulation upon suspending the cells with the cell storage medium. Cells in autologous plasma were mixed with an equal volume of heparinized phosphate-buffered saline (PBS) and centrifuged at 300×g for 3 minutes at room temperature (20°–24° C.). The supernatant was aspirated and the cell pellet gently resuspended in a cell storage medium to yield a cell suspension in a concentration as indicated above. Cell suspensions were then dispensed in 15 ml volumes into CRYOCYTE, PL2410 and PL3014 bags and stored at 4° C.

Figure 4A:
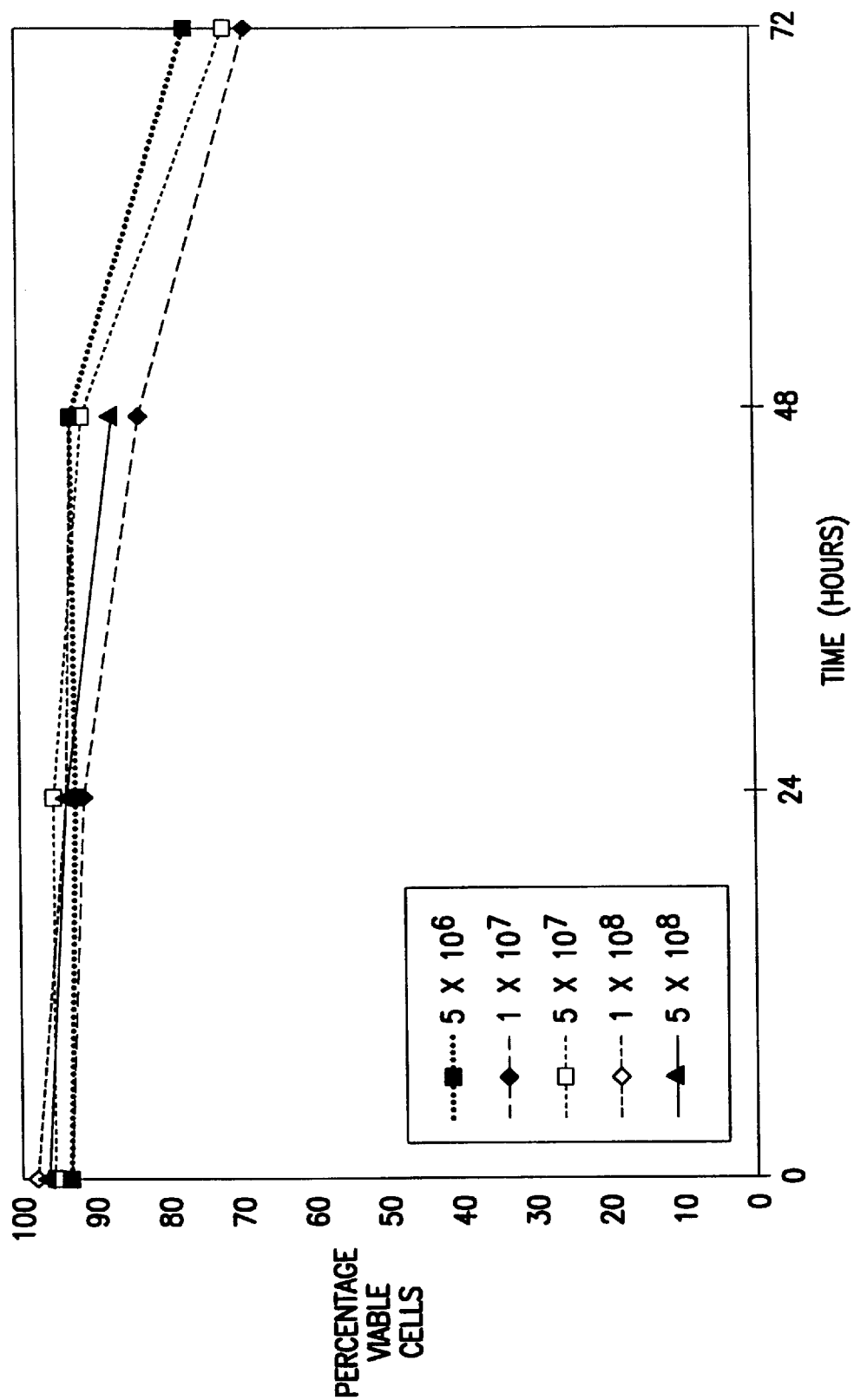
FIG. 4A shows the mean percentage, n=3, of viable nucleated cells at concentrations of $5\times10^6$, $1\times10^7$, $5\times10^7$, $1\times10^8$ and $5\times10^8$ in lactated Ringer's solution buffered with 50 mM histidine and supplemented with about 1% HSA, stored in CRYOCYTE bags over 72 hours and maintained at 40° C.
Figure 4B:
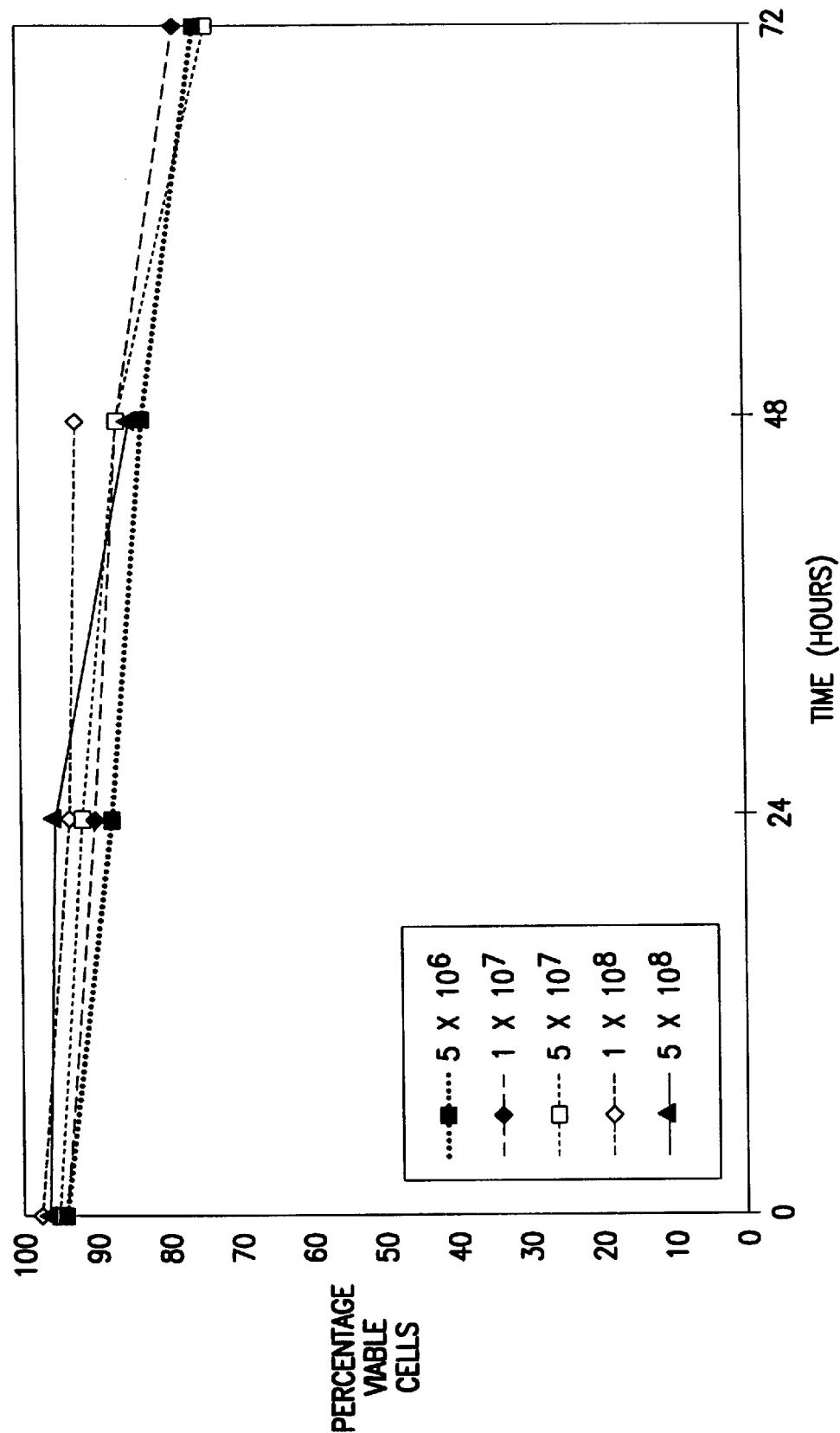
FIG. 4B shows the mean percentage, n=3, of viable nucleated cells at concentrations of $5 \times 10^6$, $1 \times 10^7$, $5 \times 10^7$, $1 \times 10^8$ and $5 \times 10^8$ in lactated Ringer's solution buffered with 50 mM histidine and supplemented with about 1% HSA, stored in PL2410 bags over 72 hours and maintained at 4° C.
Figure 4C:
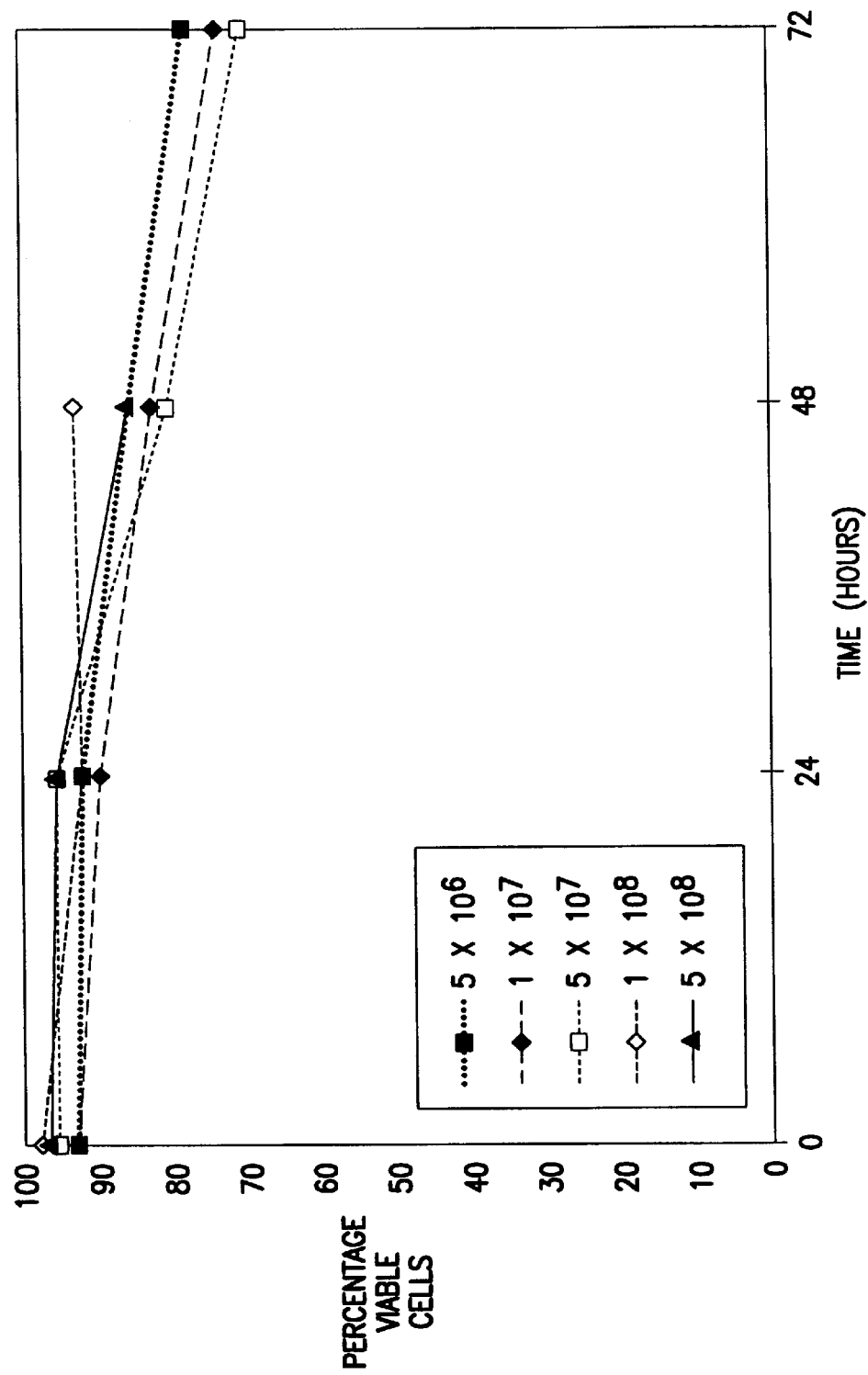
FIG. 4C shows the mean percentage, n=3, of viable nucleated cells at concentrations of $5 \times 10^6$, $1 \times 10^7$, $5 \times 10^7$, $1 \times 10^8$ and $5 \times 10^8$ in lactated Ringer's solution buffered with 50 mM histidine and supplemented with about 1% HSA, stored in PL3014 bags over 72 hours and maintained at 4° C.

FIGS. 4A, 4B and 4C show the mean percentage of viable cells at each time point for all 5 cell suspension concentrations in each storage bag tested. The 72-hour time point was eliminated for the two highest cell concentrations, $1.0\times10^8$ and $5.0\times10^8$ cells/ml of medium. The results indicate that viability was well-preserved at even the highest concentrations for up to 48 hours, never falling below 80% in any bag and remaining above 85% for 48 hours in CRYOCYTE and PL2410 bags.

The number of viable mononuclear cells remaining at each time point was also examined, however, there was no consistent effect observed from higher cell concentrations as no loss of viable mononuclear cells at higher cell concentrations were observed. The mean percentage of initial viable mononuclear cells, for any cell concentration, commonly exceeded 60% at 24 hours and were about 30–80% at 48 hours.

The mean percentage of $CD34^+/CD45^+$ cells at each time point was also determined. The results showed there was no effect of higher cell concentration.

The mean number of CFU-GM per $10^4$ mononuclear cells plated demonstrated that there was no clear evidence that higher cell concentrations were associated with a greater or more rapid loss of CFU-GM. Although the highest cell concentration, $5.0\times10^8$ cells/ml, showed a more rapid decline in CFU-GM in PL2410 and PL3014 bags, e.g., 18 CFU-GM in both bags, this same cell concentration maintained the highest level of CFU-GM in CRYOCYTE bags, e.g., 28 CFU-GM. Although the result may indicate an effect of the selected storage bag, the results more likely reflect inherent assay variability. Thus, the observed differences between the storage bags are probably not significant.

The mean number of BFU-E per $10^4$ mononuclear cells plated indicated that all cell concentrations gave similar results, e.g., about 26–43 BFU-E, although the $5.0\times10^8$ cells/ml concentration was again associated with a slightly lower number of BFU-E, e.g., 26–28 BFU-E.

The mean pH of the solution at each time point was determined. Although pH was well controlled, there was a distinct fall in the solution pH, from 7.10 to 6.95 over 48 hours, for cell concentrations at $1.0\times10^8$ and $5.0\times10^8$/ml of medium. A medium containing non-buffered lactated Ringer's solution was not tested with higher cell concentrations, but it seems likely that the change in pH would have been greater without histidine buffering.

All publications, patent and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An infusible grade storage medium for mononuclear cells consisting essentially of stem cells and an aqueous solution of about 130 mEq/liter of sodium, about 4 mEq/liter of potassium, about 109 mEq/liter of chloride, about 3 mEq/liter of calcium, about 28 mEq/liter of lactate, about 5 mEq/liter of glucose, about 1–2% human serum albumin, wherein the storage medium is buffered so that it is maintained at physiological pH, and wherein the cells are suspended therein at a concentration of about $1\times10^4$–$5\times10^8$ cells per ml of medium.

2. An infusible-grade storage medium for mononuclear cells consisting essentially of stem cells and an aqueous solution of about 140 mEq/liter of sodium, about 5 mEq/liter of potassium, about 3 mEq/liter of magnesium, about 98 mEq/liter of chloride, about 27 mEq/liter of acetate, about 23 mEq/liter of gluconate, about 1–2% human serum albumin, wherein the storage medium is buffered so that it is maintained at physiological pH, and wherein the cells are suspended therein at a concentration of about $1\times10^4$–$5\times10^8$ cells per ml of medium.

3. An infusible-grade storage medium for mononuclear cells consisting m essentially of an aqueous solution of about 130 mEq/liter of sodium, about 4 mEq/liter of potassium, about 109 mEq/liter of chloride, about 3 mEq/liter of calcium, about 28 mEq/liter of lactate, about 5 mEq/liter of glucose, about 0.1–10% human serum albumin, and an anticoagulant, wherein the storage medium is buffered so that it is maintained at physiological pH.

4. An infusible-grade storage medium for mononuclear cells consisting essentially of an aqueous solution of about 140 mEq/liter of sodium, about 5 mEq/liter of potassium, about 3 mEq/liter of magnesium, about 98 mEq/liter of chloride, about 27 mEq/liter of acetate, about 23 mEq/liter of gluconate, about 0.1–10% human serum albumin, and an anticoagulant, wherein the storage medium is buffered so that it is maintained at physiological pH.

5. An infusible-grade storage medium for mononuclear cells consisting essentially of an aqueous solution of about 140 mEq/liter of sodium, about 5 mEq/liter of potassium, about 3 mEq/liter of magnesium, about 98 mEq/liter of chloride, about 23 mEq/liter of gluconate, about 5 mEq/liter of glucose, about 0.1–10% human serum albumin, and an anticoagulant, wherein the storage medium is buffered so that it is maintained at physiological pH.

6. An infusible-grade storage medium for mononuclear cells consisting essentially of an aqueous solution of about 130 mEq/liter of sodium, about 4 mEq/liter of potassium, about 109 mEq/liter of chloride, about 3 mEq/liter of calcium, about 27 grams/liter of acetate, about 5 mEq/liter of glucose, about 0.1–10% human serum albumin, and an anticoagulant, wherein the storage medium is buffered so that it is maintained at physiological pH.

7. An infusible-grade storage medium for mononuclear cells consisting essentially of an aqueous solution of about 140 mEq/liter of sodium, about 103 mEq/liter of chloride, about 5 mg/deciliter of calcium, about 3 mg/deciliter of magnesium, about 55 mEq/liter of acetate., about 0.1–10% human serum albumin, and an anticoagulant, wherein the storage medium is buffered so that it is maintained at physiological pH.

8. An infusible-grade storage medium for mononuclear cells consisting essentially of an aqueous solution of about 4 g/liter potassium chloride, about 600 mg/liter potassium phosphate monobasic, about 80 g/liter sodium chloride, about 475 mg/liter sodium phosphate dibasic, about 10 g/liter of glucose, about 0.1–10% human serum albumin, and an anticoagulant, wherein the storage medium contains no phenol red and is buffered so that it is maintained at physiological pH.

9. An infusible suspension of mononuclear cells in a solution consisting essentially of an electrolyte replenisher base solution and about 0.1–10% human serum albumin, wherein the suspension is buffered so that it is maintained at physiological pH.

10. The suspension of claim 9, which further comprises an anticoagulant.

11. A method for preserving mononuclear cells comprising:

(a) suspending said mononuclear cells in a solution consisting essentially of an infusible-grade electrolyte replenisher base solution and about 0.1–10% human serum albumin, wherein the solution is buffered so that it is maintained at physiological pH, to yield a stable cell suspension, comprising about $1\times10^4$–$5\times10^8$ cells per ml of solution; and (b) maintaining the cell suspension at a temperature of about 4° C. to 24° C.

12. The method of claim 11, wherein the solution contains an anticoagulant.

13. The suspension of claim 10, wherein the anticoagulant is selected from the group consisting of heparin, anticoagulant citrate phosphate dextrose adenine solution (ACDA), acid citrate dextrose (ACD), citrate phosphate dextrose adenine solution (CPD), and sodium citrate.

14. The method of claim 12, wherein the anticoagulant is selected from the group consisting of heparin, anticoagulant citrate phosphate dextrose adenine solution (ACDA), acid citrate dextrose (ACD), citrate phosphate dextrose adenine solution (CPD), and sodium citrate.

15. The suspension of claim 9, wherein the solution contains about 1–2% human serum albumin.

16. The method of claim 11, wherein the solution contains about 1–2% human serum albumin.

17. The suspension of claim 9, wherein the mononuclear cells are suspended therein at a concentration of about $1\times10^4$–$5\times10^8$ cells per ml of solution.

18. The method of claim 11, comprising prior to step (a) isolating the cells from a mammalian donor sample or blood product by density gradient separation or a heparinized phosphate buffered saline wash (PBS).

19. The method of claim 18, further comprising, after isolation, concentrating the cells by centrifugation.

20. The suspension of claim 9, wherein the cells are suspended to EL concentration of about $2$–$5\times10^7$ cells per ml of solution.

21. The method of claim 11, wherein the cells are suspended to a concentration of about $2$–$5\times10^7$ cells per ml of solution.

22. The suspension of claim 9, wherein the solution is buffered with histidine so that it is maintained at physiological pH.

23. The method of claim 11, wherein the solution is buffered with histidine so that it is maintained at physiological pH.

24. The suspension of claim 9, wherein the mononuclear cells are stem cells.

25. The suspension of claim 10, wherein the mononuclear cells are stem cells.

* * * * *

UNITED STATES PATENT AND TRADEMARK OFFICE
CERTIFICATE OF CORRECTION

PATENT NO.    : 6,277,557 B1
DATED         : August 21, 2001
INVENTOR(S)   : Scott Robert Burger, Allison Hubel and John Jeffrey McCullough It is certified that error appears in the above-identified patent and that said Letters Patent is hereby corrected as shown below:

Column 2,
Line 48, delete "Contain" and insert -- contain --, therefor.

Column 4,
Lines 7 and 67, delete "40C." and insert -- 4°C. --, therefor.

Column 6,
Line 13, delete "pHI" and insert -- pH --, therefor.
Line 20, delete "X-VfVO" and insert -- X-VIVO --, therefor.

Column 7,
Line 1, delete "unit(s)/mi" and insert -- unit(s)/ml --, therefor.

Column 9,
Line 33, insert -- Cells -- after "Hematopoietic Stem".

Column 10,
Line 55, delete "31" after "*Transfusion*" and insert -- 36: --, therefor.

Column 12,
Line 3, delete "7:" after "*Blood*" and insert -- 70: --, therefor.

Column 14,
Line 52, delete "3D" after "3A," and insert -- 3B --, therefor.

Column 15,
Line 22, delete "104" and insert -- $10^4$ --, therefor.
Line 47, delete "sonl." after "Ringer's" and insert -- soln. --, therefor.

Column 18,
Line 12, delete "m" after "consisting".
Line 46, delete "." after "acetate".

UNITED STATES PATENT AND TRADEMARK OFFICE
CERTIFICATE OF CORRECTION

PATENT NO. : 6,277,557 B1
DATED : August 21, 2001
INVENTOR(S) : Scott Robert Burger, Allison Hubel and John Jeffrey McCullough It is certified that error appears in the above-identified patent and that said Letters Patent is hereby corrected as shown below:

Column 20,
Line 10, delete "EL" and insert -- a --, therefor.

Signed and Sealed this

Thirtieth Day of April, 2002

Attest:

JAMES E. ROGAN
*Attesting Officer*    *Director of the United States Patent and Trademark Office*